US007135624B2

(12) United States Patent
Bryan et al.

(10) Patent No.: US 7,135,624 B2
(45) Date of Patent: Nov. 14, 2006

(54) ENZYMES INVOLVED IN TRITERPENE SYNTHESIS

(75) Inventors: Gregory T. Bryan, Wilmington, DE (US); Brian McGonigle, Wilmington, DE (US); Carl A. Maxwell, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 228 days.

(21) Appl. No.: 10/221,074

(22) PCT Filed: Mar. 9, 2001

(86) PCT No.: PCT/US01/07611

§ 371 (c)(1),
(2), (4) Date: Sep. 9, 2002

(87) PCT Pub. No.: WO01/66773

PCT Pub. Date: Sep. 13, 2001

(65) Prior Publication Data

US 2003/0208791 A1    Nov. 6, 2003

(51) Int. Cl.
*C12N 15/29* (2006.01)
*C12N 15/52* (2006.01)
*C12N 15/82* (2006.01)

(52) U.S. Cl. ............... 800/298; 800/278; 800/285; 800/306; 800/312; 435/419; 435/320.1; 536/23.1; 536/23.2; 536/23.6

(58) Field of Classification Search ............ 800/278, 800/279, 285, 286, 287, 298; 536/23.1, 23.2, 536/23.6; 435/320.1, 419
See application file for complete search history.

(56) References Cited

FOREIGN PATENT DOCUMENTS

WO   WO 95/30009 A2   11/1995
WO   WO 01/46391 A2   6/2001

OTHER PUBLICATIONS

GenBank Accessions AB014057 and AB009030.*
Kushiro T. et al. Eur. J. of Biochemistry, 1998; vol. 256, No. 1, pp. 238-244.*
Wu T. et al. Biochemistry, 2002; vol. 41 pp. 8238-8244.*
Masakazu Shiraiwa et. al., Agric. Biol. Chem., vol. 55:323-331, 1991, Composition and Content of Saponins in Soybean Seed According to Variety, Cultvation Year and Maturity.
Kazuyoshi Okubo et. al., Biosci. Biotech. Biochem., vol. 56:99-103, 1992, Components Responsible for the Undesirable Taste of Soybean Seeds.
National Center for Biotechnology Information General Identifier No. 3721856, Oct. 9, 1998, Kushiro, T. et. al., Molecular Cloning of Oxidosqualene Cyclase CDNA From Panax Ginseng: The Isogene that Encodes Beta-Amyrin Synthase.
National Center for Biotechnology Information General Identifier No. 3688600, Oct. 3, 1998, Kushiro, T. et. al., Beta-Amyrin Synthase-Cloning of Oxidosqualene Cyclase That Catalyzes the Formation of the Most Popular Triterpene Among Higher Plants.
National Center for Biotechnology Information General Identifier No. 3779033, Oct. 22, 1998, Rounsley, S.D. et. al., *Arabidopsis thaliana* Chromosome II Bac T4E14 Genomic Sequence.
National Center for Biotechnology Information General Identifier No. 5606831, Jul. 27, 1999, Shoemaker, R. et. al., Public Soybean EST Project.
Accession No. AB009030, Oct. 5, 1998, Kushiro T. et. al, Cloning of Oxidosqualene Cyclase That Catalyzes the Formation of the Most Popular Triterpene Among Higher Plants.
Tetsuo Kushiro et. al., Eur. J. Biochem., vol. 256:238-244, 1998, Cloning of Oxidosqualene Cyclase That Catalyzes the Formation of the Most Popular Triterpene Among Higher Plants.
Masaaki Shibuya et. al., Eur. J. Biochem., vol. 266:302-307, 1999, Two Branches of the Lupeol Synthases Gene in the Molecular Evolution of Plant Oxidosqualene Cyclases.
Hiroaki Hayashi et. al., Biol. Pharm. Bull., vol. 23-231-234, 2000, Molecular Cloning and Characterization of a Cdna for Glycyrrhiza Glabra Cycloartenol Synthase.
Database Accession No. 94:267952, 1994, C. Tsukamoto et al., ACS Symposium Series—General Review—Journal, Genetic Improvement of Saponin Components in Soybean.
Chigen Tsukamoto et. al., Phytochemistry, vol. 34:1351-1356, 1993, Genetic and Chemical Polymorphisms of Saponins in Soybean Seed.
Akio Kikuchi et. al., Breeding Science, vol. 49:167-171, 1999, Inheritance and Characterization of a Null Allele for Group a Acetyl Saponins Found in a Mutant Soybean (*Glycine Max* (L) Merrill).
Chigen Tsukamoto et. al., J. Agric. Food Chem., vol. 43:1184-1192, 1995, Factors Affecting Isoflavone Content in Soybeans Seeds: Changes in Isoflavones, Saponins, and Composition of Fatty Acids at Different Temperatures During Seed Development.
Yumiko Yoshiki et. al., Biosci. Biotechnol. Biochem., vol. 62:2291-2299, 1998, Relationship Between Chemical Structures and Biological Activities of Triterpenoid Saponins From Soybean.
Edmund W. Lusas et. al., Journal of Nutrition, vol. 125:573S-580S, 1995, Soy Protein Products: Processing and Use.
Thomas J. Bach et. al., Progress in Lipid Research, vol. 36:197-226, 1997, Cloning of CDNAS or Genes Encoding Enzymes of Sterol Biosynthesis From Plants and Other Eukaryotes: Heterologous Expression and Complementation Analysis of Mutants for Functional Characterization.
Tung-Kung Wu et al., Conversion of a Plant Oxidosqualene-Cycloartenol Synthase to an Oxidosqualene-Lanosterol Cyclase by Random Mutagenesis, Biochemistry, 2002, vol. 41:8238-8244.
Ikuro Abe et al., Active Site Mapping of Affinity-labeled Rat Oxidosqualene Cyclase, The Journal of Biological Chemistry, Jan. 14, 1994, vol. 269, No. 2:802-804.

(Continued)

Primary Examiner—Russell P. Kallis

(57) ABSTRACT

This invention relates to an isolated nucleic acid fragment encoding an oxidosqualene cyclase. The invention also relates to the construction of a chimeric gene encoding all or a portion of the isolated polynucleotides of the invention, in sense or antisense orientation, operably linked to a suitable regulatory sequence.

21 Claims, 5 Drawing Sheets

OTHER PUBLICATIONS

Karl Poralla et al., A specific amino acid repeat in squalene and oxidosqualene cyclases, Elsevier Science Ltd., Apr. 1994, 157-158.
EMBL Sequence Database, Accession No. 082140, Nov. 1, 1998, T. Kushiro et al., Beta-Amyrin Synthase—Cloning of Oxidosqualene Cyclase That Catalyzes the Formation of the Most Popular Triterpene Among Higher Plants, XP-002170235.
EMBL Sequence Database, Accession No. A1900929, Jul. 28, 1999, R. Shoemaker et al. Public Soybean EST Project, XP-002170236.
K. Papadopoulou et al., Compromised Disease Resistance in Saponin-Deficient Plants, PNAS, vol. 96, No. 22:12923-12928, Oct. 26, 1999.

Song You et al., Molecular Cloning and Sequencing of an Allium Macrostemon cDNA Probably Encoding Oxidosqualene Cyclase, Plant Biotechnology, 16 (4):311-214, 1999.
EMBL Sequence Database, Accession No. Q9SSZ2, May 1, 2000, S. You et al., Molecular Cloning and Sequencing of an Allium Macrostemon CDNA Probably Encoding Oxidosqualene Cyclase, XP-002170238.
EMBL Sequence Database, Accession No. AF169966, Oct. 21, 1999, L. B. Darr et al., A Rice CDNA Similar to Cycloartenol Synthase, XP-002170239.

* cited by examiner

Figure 1A

```
             *  *          *   **  ** *       ****                  *        *        *     *
SEQ ID NO:12   MWKLKIAEGNKNDPYLYSTNNFVGRQTWEFDPDYVASPGELEEVEQVRRQFWDNRYQVKP
SEQ ID NO:13   MWRLMTAKGG-NDPYLYSTNNFIGRQTWEFDPDY-GTPAERAEVEEARLHFWNNRYQVKP
SEQ ID NO: 2   MWRLKIADGGK-DPYIFSTNNFVGRQTWEFDPE-AGTPEERAQVEAARQNFYNNRFKVKA
SEQ ID NO: 4   MWRLKIADGGN-DPYIFSTNNFVGRQTWEFDPE-AGSPEERAQVEAARQHFYHNRFKVKP
SEQ ID NO: 6   MWRLKIADGGN-DPYIFSTNNFVGRQTWEFDSE-AGTAEERAQIEAARQNFYENRFMVKA
SEQ ID NO: 8   MWRLKVSEGG--GPWLRSVNNFLGRAVWEFDPDY-GTPEERAEVKRVRREFTDRRFEKKE
                                                                         60
                1

*    *  *       *       *               *       ** ***** *
SEQ ID NO:12   SGDLLWRMQFLREKNFRQTIP-QVKVGDDEAVTYEAATTTLRRAVHFFSALQASDGHWPA
SEQ ID NO:13   SSDVLWRMQFLKEKNFKQIIP-QVKVEDGEEITYEAATTTLRRAVHYFSALQADDGHWPA
SEQ ID NO: 2   CGDLLWRFQILREKNFKQSIP-SVKIEDGEEITYEKVISTLRRAAHHLSALQTSDGHWPA
SEQ ID NO: 4   CADLLWRFQVLRENNFKQTIP-RVTIEDGEEITYQKVTSAVRRGAHHLAALQTSDGHWPA
SEQ ID NO: 6   CGDRLWRFQILRENNFKQTIS-GVKIEDDEKITCEKIRSTMKRATHYLSSLQTSDGHWPA
SEQ ID NO: 8   SQDLLMRMQYAKEKHLQVDLPA-IKLADSAQVTEETLLTSLRRCLSQHSALQAHDGHWAG
                                                                         120
                61

*  *       *                      **   *  *  *  * * *****  *  **
SEQ ID NO:12   ENSGPLFFLPPLVMCVYITGHLDTVFPAEHRKEILRYIYCHQNEDGGWGLHIEGHSTMFC
SEQ ID NO:13   ENAGPLFFLPPLVMCLYITGHLNTVFPAEHRIEILRYIYCHQNDDGGWGLHIEGHSTMFC
SEQ ID NO: 2   QIAGPLFFLPPLVFCMYITGHLDLVFPEEYRKEILRYIYYHQNEDGGWGLHIEGHSTMFG
SEQ ID NO: 4   QIAGPLFFLPPLVFCMYITGNLESVFPEEHRKEILRYTYYHQNEDGGWGLHIEGHSTMFC
SEQ ID NO: 6   HLGGSLFFTPPLVICLYITGHIDSIFSEEYRKEILRYIYYHQNKDGGWGLHIEGHSIMFC
SEQ ID NO: 8   DFSGILFIMPILIFALHVTGSLNTVLSTEHRCEICRYIYNHQNEDGGWGTQVLGPSTMFG
                                                                         180
                121
```

Figure 1B

```
SEQ ID NO:12    TTLSYICMRILGEGPDGGVNNACARGRKWILDHGSVTAIPSWGKTWLSILGVYEWIGSNP
SEQ ID NO:13    TALSYICMRILGEGRDGGENNACARARKWILDHGSVTAIPSWGKTWLSILGLFDWSGSNP
SEQ ID NO:2     TTLNYICMRILGEGPNGGHENACARGKKWIHDHGGVTHIPSWGKTWLSILGVFDWCGSNP
SEQ ID NO:4     TALNYICMRMLGEGPNGGHDNACARARKWIRDHGGVTHIPSWGKTWLSILGVFDWCGSNP
SEQ ID NO:6     TTLNYICMRILGEGPNGGHNNACAKARKWIHDHGGATHIPSWGKFWLSVLGIVDWCGSNP
SEQ ID NO:8     SCLNYVTLRLLGEV---ENDALTKGRAWILLRGSATAIPQWGKIWLSVVGLYEWSGNNS
                                                                          240
                  *  * ****   *         *    * ****  *     ***   **   *  * *

SEQ ID NO:12    MPPEFWILPSFLPMHPAKMWCYCRMVYMPMSYLYGKRFVGPITPLILQLREELYGQPYNE
SEQ ID NO:13    MPPEFWILPPFLPMHPAKMWCYCRMVYMPMSYLYGKRFVGPITPLILQLREELYAQAYDE
SEQ ID NO:2     MPPEFWILPSFLPMHPAKMWCYCRLVYMPMSYLYGKRFVGPITPLILQLREELFTQPYEK
SEQ ID NO:4     MPPEFWILPSFLPMHPAKMWCYCRLVYMPMSYM-GKGFVGPITPLILQLREELFTQPYEK
SEQ ID NO:6     MPPEFWILPSFLPMHPGKMWCYCRLVYMPMSYLYGKKFTGPITPLVVNLREELFIQPYDE
SEQ ID NO:8     IIPELWLVPYFLPIHPGRFWCFCRLVYMPMSYLYGKKFVGPITPTIVAIREELYSVSYSE
                                                                          300
                 ** * ****  ** ** ** ** ********** **  *****    ****

SEQ ID NO:12    INWRKTRRVCAKEDIYYPHPLIQDLLWDSLYVLTEPLLTRWPFNKL-REKALQTTMKHIH
SEQ ID NO:13    INWRKVRHNCAKEDLYYPHPLIQDLLMWDSLYIFTEPFLTRWPFNKL-REKALQTTMKHIH
SEQ ID NO:2     VNWKKVRHQCAKEDLYYPHSLIQDLVWDSLYMFTEPLLTCWPFNKLIREKALQVTMNHIH
SEQ ID NO:4     VNWKKARHQCAKEDLYYPHPLIQDLIWDSLYIFTEPLLTRWPFNKLIREKALQVTMKHIH
SEQ ID NO:6     NSWKKARHKCANEDLYYPHHWIQDLLWDSLYVFTEPLLNCWPFNKLVREKALQVTMKHIH
SEQ ID NO:8     IDWNKARDTCAKEDLRYPRSLLQNVIWTCLNKFVEPVLNCWPINKL-RDTALKNLMKHIH
                                                                          360
                  * *    * ***  **   *  *  ***   **  *   **  **     *  ****
```

Figure 1C

```
                    ****  **    * * ***    ** ** *  **  ****  *    *
SEQ ID NO:12        YEDENSRYITIGCVEKVLCMLVCWVEDPNGDYFRKHLARIPDYIWVAEDGMKMQSF-GSQ
SEQ ID NO:13        YEDENSRYITIGCVEKVLCMLACWVEDPNGDYFKQHLARIPDYIWVAEDGMKMQSF-GSQ
SEQ ID NO: 2        YEDENSRYITIGCVEKVLCMLACWVEDPQGDAFKKHLARVSDYLWVSEDGMTMQSF-GSQ
SEQ ID NO: 4        YEDETSRYITIGCVEKVLCMLACWVEDPNGDAFKKHLARVPDYLWVSEDGMTMQSF-GSQ
SEQ ID NO: 6        YEDENSRYIAIGCVEKVLCMLACWVEDPNGDAFKKHLARIPDYLWVSEDGMTMQI-GTQ
SEQ ID NO: 8        YEDESTKYIGVCPINKALDMICCWSEDPNSDALKLHLPRIYDYLWLAEDGMKAQVYDGCQ
                361                                                          420

*   *             * *  ***   *** **     **   *****
SEQ ID NO:12        EWDTGFSIQALLDSDLTHEIGPTLMKGHDFIKKSQVKDNPSGDFKSMYRHISKGSWTFSD
SEQ ID NO:13        EWDTGFAIQALLASDLIDEIRPTLMKGHDFIKKSQVKENPSGDFKSMHRHISKGSWTFSD
SEQ ID NO: 2        EWDAGFAVQALLATKLIDEIGHSLAKGHDFIKKSQVRDNPSGDFKSMYRHITKGSWTFSD
SEQ ID NO: 4        EWDAGFAVQALLATNIIEEIGPTFAKGHDFIKKSQVKDNPFGDFKSMHRHISKGSWTFSD
SEQ ID NO: 6        SWDVGFIVQALLATNLIDDFGPTIAKAHDFIKKSQVRENPSGDFKSMYRHICKGSWTLAD
SEQ ID NO: 8        SWELAFIVQAYCSTDLVNEFGPTLRKAHEFIKSSQVLENHPNS-ETYYRHRSKGSWTLST
                421                                                          480

*  ***  ***    **        **         *               *
SEQ ID NO:12        QDHGWQVSDCTAEGLKCCLIFSTMPEEIVGKKIKPERLYDSVNVLLSLQRKNGGLSAWEP
SEQ ID NO:13        QDHGWQVSDCTAEALKCCLLFSRMPTEIVGDKMEDNQLFDAVNMLSLQSKNGGLAAWEP
SEQ ID NO: 2        QDHGWQVSDCTAEGLKCCLLLSKLSPEIVGEKVKPERFYDSVNILLSLQSKKGGIAAWEP
SEQ ID NO: 4        QDHGWQVSDCTAEGLKCCLLLSMLPPEIVGEKMEPERLYDSVNVLLSLQSKKGGLAAWEP
SEQ ID NO: 6        RDHAWQVSDTTAECLKCCLKCCLLLSVLPQDIVGEKMELEKLHDSINLILSLQSKNGGMTAWEP
SEQ ID NO: 8        ADNGWSVSDCTAEALKALLLSKISPNLVGDPVKGERLHDAVDCLLSFMNKDGTFSTYEC
                481                                                          540
```

Figure 1D

```
                                                                    *  * **** *    *** *  *** ** ** *
SEQ ID NO:12   AGAQEWLELLNPTEFFADIVIEHEYVECTSSAIQALVLFKKLYPGHRKKEIDNFITNAVR
SEQ ID NO:13   AGSSEWLELLNPTEFFEDIVIEHEYVECTSSAIQAMVMFKKLYPGHRKKEIEVSITNAVQ
SEQ ID NO: 2   IGAQEWLELLNPTEFFEDIVIEHEYVECTGSAIQALVLFQKLYPEHRKTEIKNFIVNAVQ
SEQ ID NO: 4   AGAQEWLELLNPTEFFADIVVEHEYVECTGSAIQALVLFKKLYPGHRKKEIENFITNAVR
SEQ ID NO: 6   AGAYKWLELLNPTEFFADIVEHEYLECTASAIQVLVLFKKLYPEHRKEEIENFIAKAVT
SEQ ID NO: 8   KRTTSLLEVLNPSESFLNIIVDYPSVECTSSVLQALIMFKELYPGYRKEEIGKCIKNASK
               541                                                         600

** *   ** ****    *  *  ****  ***    ** * * * ****   **
SEQ ID NO:12   YLEDTQMPDGSWYGNWGVCFTYGSWFALGGLAAAGKTYYNCAAVRKAVEFLLKSQMDDGG
SEQ ID NO:13   YLEDIQMPDGSWYGNWGVCFTYGTWFAMGGLTAAGKTYNNCQTLHKAVDFLIKSQRSDGG
SEQ ID NO: 2   FLEDTQTTNGSWYGCWGVCFTYGSWFALGGLAAAGKTYTNCNAIRKAVKFLLTTQREDGG
SEQ ID NO: 4   FLEDTQTADGSWYGNWGVCFTYGSWFALGGLAAAGKTYTNCAAIRKAVKFLLTTQREDGG
SEQ ID NO: 6   FIEDTQLENGSWYGNWAVCFTYSSWFALGGLVAAGKTYTNCVTIRKAVKFLLKIQNKDGG
SEQ ID NO: 8   FIEDKQRKDGSWFGTWGICFTYGTFFGVKGLIASGRTYENSSSIRKACNFLLSKQLSTGG
               601                                                         660

********       *                    *         *  ** **** *
SEQ ID NO:12   WGESYLSCPKKVYVPLEGNRSNLVHTGWALMGLIHSEQAERDPTPLHRAAKLLINSQMED
SEQ ID NO:13   WGESYLSCPNKEYTPLEGNRSNLVHTSWAMMGLIHSRQAERDPTPLHRAAKLLINSQMES
SEQ ID NO: 2   WGESYLSSPKKIYIPLEGSRSNVVQTAWALMGLIYAGQSERDLTPLHRAAKLTPLHRAAKLLINSQLEE
SEQ ID NO: 4   WGESYLSSPKKIYVPLEGSRSNVHTAWALMGLIHAGQADRDPMPLHRAAKLLINSQLEE
SEQ ID NO: 6   WGESYLSCPRKMYVPLEGSRSNVVQTSWALMALIHAEQAERDPTPLHHAAKLLINSQLED
SEQ ID NO: 8   WGESYLSSETEAYV--EATSPHAVNTAWAMLALIYAGVERDPTPLHAAKELINMQLET
               661                                                         720
```

Figure 1E

```
                 *    ****         *          **   * **** *            *
SEQ ID NO:12    GDFPQQEISGVFMKNCMLHYAAYRNIYPLWALAEYRRRVPLPSLGT
SEQ ID NO:13    GDFPQQEITGVFMKNCMLHYAASRNIYPLWALAEYRKNVRLPSKSV
SEQ ID NO: 2    GDWPQQEITGVFLKNCMMHYPMYRNIFPMWALAEYRRRVPLPSTEG
SEQ ID NO: 4    GDWPQQEITGVFMKNCMLHYPMYRDIYPMWALAEYRRRVPLPSTEV
SEQ ID NO: 6    GDWPQQETLGVYLRNCLVHYSFYRNIFPMWALAEYRTNVLLPSFTI
SEQ ID NO: 8    GEFPQQEHVGCFNCSIYFNYGNYRNLYPIWALGEFRRRL-LAKN-
                721                                              767
```

ENZYMES INVOLVED IN TRITERPENE SYNTHESIS

FIELD OF THE INVENTION

This invention is in the field of plant molecular biology. More specifically, this invention pertains to nucleic acid sequences encoding enzymes involved in the cyclization of squalene epoxide to form the ring structure precursor to triterpenes, including sterols and saponins, in plants and seeds. This invention also includes transgenic plants where the expression of the nucleic acids of the present invention results in altered levels of triterpenes, including sterols and saponins. Also included in the invention are protein products and food and dietary supplement applications.

BACKGROUND OF THE INVENTION

The terpenoids, also called isoprenoids, constitute the largest family of natural products with over 22,000 individual compounds of this class having been described. The terpenes or terpenoids (hemiterpenes, monoterpenes, sesquiterpenes, diterpenes, triterpenes, tetraterpenes, polyprenols, and the like) play diverse functional roles in plants as hormones, photosynthetic pigments, electron carriers, mediators of polysaccharide assembly, and structural components of membranes. The majority of plant terpenoids are found in resins, latex, waxes, and oils.

Two molecules of farnesyl pyrophosphate are joined head-to-head to form squalene, a triterpene, in the first dedicated step towards sterol biosynthesis. Squalene is then converted to 2,3-oxidosqualene which, in photosynthetic organisms, may be converted to the 30 carbon, 4 ring structure, cycloartenol or to the 5 ring homolog, β-amyrin, a sapinogenin precursor. This conversion step is catalyzed by one of at least two oxidosqualene cyclases: cycloartenol synthase or β-amyrin synthase.

Cycloartenol is formed by the enzyme cycloartenol synthase (EC 5.4.99.8), also called 2,3-epoxysqualene-cycloartenol cyclase. The basic nucleus of cycloartenol can be further modified by reactions such as desaturation or demethylation to form the common sterol backbones such as stigmasterol and sitosterol, which can be modified further.

The β-amyrin cyclization activity is distinct from cycloartenol synthase (Kushiro, T., et al. (1998) *Eur. J. Biochem.* 256:238–244). β-amyrin synthase catalyzes the cyclization of 2,3-oxidosqualene to β-amyrin. Yet, the basic β-amyrin ring structure may be modified in much the same manner as is the cycloartenol structure to give classes of sapogenins. Saponins are glycosylated sapogenins and may play a pathogen defense role in plant tissues.

Soybean seeds, for example, contain several classes of saponins, all of which are formed from one sapogenin ring structure that is modified by hydroxylation and by different carbohydrate moieties. Total saponin content varies somewhat by soybean cultivar but is in the range of 0.25% of the seed dry weight (Shiraiwa, M., et al. (1991) *Agric. Biol. Chem.* 55:323–331).

The name saponin was derived from their strong foaming power. The physiological function of saponins in soybean seeds is not clear, but they do contribute to the bitter or astringent flavor of soybean seeds (Okubo, K., et al. (1992) *Biosci. Biotechnol. Biochem.* 56:99–103). Saponins are thought to have cholesterol-lowering effects and reduction in colon cancer risk. Besides imparting undesirable flavors to feed and foods, saponins have been shown to have hemolytic action against red blood cells. Soybeans are also involved in the reduction of hot flashes in postmenopausal women, lowering the risk of hormone-related cancer, slowdown of bone loss in osteoporosis and improvement in vascular health. Saponins are believed to be involved in these beneficial soybean effects.

A variety of processed vegetable protein products are produced from soybean. These range from minimally processed, soy beans and soy nuts such as toasted soy nuts and defatted items such as soybean meal, grits, and flours to more highly processed items such as soy protein concentrates and soy protein isolates. In other soy protein products, such as full-fat soy flour, the oil is not extracted. In addition to these processed products, there are also a number of specialty products based on traditional Oriental processes, which utilize the entire bean as the starting material. Examples include soy milk, soy sauce, tofu, natto, miso, tempeh, and yuba.

Examples of use of soy protein products in human foods include applying soy protein concentrates and soy protein isolates in nutritional beverage, emulsified meat and whole muscle meat applications; textured soy protein in meat analogues; soy protein isolates in infant formula. Facilities and methods to produce protein concentrates and isolates from soybeans are available across the world. To the extent that they are retained in these processed soy fractions and the foods prepared from them, the saponin content of the starting beans influences the flavor of the food.

Sequences of two different β-amyrin synthase isoforms has been described for Korean ginseng (*Panax ginseng*; NCBI General Identifier Nos. 3721856 and 3688600). A soybean EST having NCBI General Identification No. 5606831 has been identified with and is "similar to the ginseng sequence," according to the NCBI entrez.

Identification of the genes encoding oxidosqualene cyclases in a variety of crops will allow the manipulation of the same. Interference with triterpenoid ring synthesis during plant development may be expected to decrease the total content of saponins in plant parts resulting in foods with increased nutritional value, and better flavor.

SUMMARY OF THE INVENTION

The instant invention relates to isolated nucleic acid sequences encoding enzymes involved in triterpene synthesis. Specifically, this invention concerns isolated nucleic acid sequences encoding oxidosqualene cyclase enzymes.

The present invention relates to an isolated polynucleotide comprising a nucleotide sequence selected from the group consisting of: a first nucleotide sequence encoding a polypeptide of at least 100 amino acids having at least 80% identity based on the Clustal method of alignment when compared to a polypeptide selected from the group consisting of SEQ ID NOs:2, 4, 6, and 8; and a second nucleotide sequence comprising the complement of the first nucleotide sequence. The present invention also relates to an isolated polynucleotide comprising a nucleotide sequence having at least 30 contiguous nucleotides derived from a nucleic acid sequence selected from the group consisting of SEQ ID NOs:1, 3, 5, and 7 and the complement of such sequences. An isolated polypeptide of at least 100 amino acids that has at least 80% identity based on the Clustal method of alignment when compared to a polypeptide selected from the group consisting of SEQ ID NOs:2, 4, 6, and 8 is also an embodiment of the subject invention.

In another embodiment, the instant invention relates to a chimeric polynucleotide comprising the isolated polynucleotide of the present invention operably linked to suitable a regulatory sequence.

In a further embodiment, the instant invention concerns an isolated host cell comprising the chimeric polynucleotide of the present invention. The host cell may be selected from the group consisting of a yeast cell, a bacterial cell, and a plant cell. The present invention also relates to a virus comprising a chimeric gene encoding the polypeptide of the present invention.

Compositions, including plants and plant parts, comprising the isolated poypeptide or polynucleotide of the present invention are also embodied by the present invention. The invention also includes transformed plants that arise from transformed host cells of higher plants and seeds or grains derived from such transformed plants. Such transgenic plant includes those having an altered level of a triterpenoid, such as β-amyrin.

The present invention is also directed to an isolated soy protein and a food product. The food product may be selected from the group consisting of a soy protein product, soybean meal, soy flour, soy protein concentrate, soy milk, a dietary supplement, nuts, tofu, natto, miso, and tempeh.

The present invention also relates to a method of altering the level of expression of an oxidosqualene cyclase polypeptide in a plant cell, which comprises: constructing an isolated polynucleotide comprising a nucleotide sequence of at least 30 contiguous nucleotides derived from an isolated polynucleotide of the present invention; introducing the isolated polynucleotide into a plant cell; measuring the level of oxidosqualene cyclase in the plant cell containing the polynucleotide; and comparing the level of oxidosqualene cyclase in the plant cell containing the isolated polynucleotide with the level of oxidosqualene cyclase in a plant cell of the same species as the plant cell of step (b) that does not contain the isolated polynucleotide.

Another embodiment of the present invention is a method of producing a plant with altered levels of oxidosqualene cyclase comprising: transforming a plant cell with the chimeric polynucleotide of the present invention; growing the transformed plant cell from step (a) under conditions that promote the regeneration of a whole plant from the transformed cell, wherein the plant regenerated from the transformed cell produces an amount of oxidosqualene cyclase that is greater than the amount of the oxidosqualene cyclase that is produced in a plant that is regenerated from a plant cell of the same species as the plant of step (a) that is not transformed with the chimeric polynucleotide; and optionally transforming the plant cell of step (a) with a second chimeric polynucleotide comprising a nucleic acid sequence encoding a polypeptide that regulates expression of at least one enzyme of the triterpenoid pathway; and growing the transformed plant cell from step (c) under conditions that promote the regeneration of a whole plant from the transformed cell; wherein the plant regenerated from the transformed cell produces an amount of oxidosqualene cyclase that is greater than the amount of the oxidosqualene cyclase that is produced in a plant that is regenerated from a plant cell of the same species as the plant of step (c) that is not transformed with the chimeric polynucleotide of claim 5 and a second chimeric polynucleotide.

The present invention also relates to: (1) a method of making a soy protein product comprising processing the grain of the present invention, said processing including: toasting or cracking said grain to remove the meats from the hulls; and flaking the meats obtained in step (a) to obtain a desired flake thickness, and (2) a method for positive selection of a transformed cell comprising: transforming a host cell with the chimeric gene of the present invention; and growing the transformed host cell under conditions which allow expression of the oxidosqualene cyclase polynucleotide in an amount sufficient to complement a null mutant to provide a positive selection means.

The improved palatability due to the suppression of saponin expression is also included. Included are also products, with improved palatability, prepared using soybeans having lower amounts of saponins due to the presence of a chimeric gene containing the sequences of the present invention.

BRIEF DESCRIPTION OF THE FIGURE AND SEQUENCE LISTINGS

The invention can be more fully understood from the following detailed description and the accompanying Sequence Listing which form a part of this application.

The following sequence descriptions and Sequence Listing attached hereto comply with the rules governing nucleotide and/or amino acid sequence disclosures in patent applications as set forth in 37 C.F.R. §1.821–1.825.

FIG. 1A–E depicts the amino acid sequence alignment between the oxidosqualene cyclases encoded by soybean clones sdp3c.pk020.o10 (SEQ ID NO:2), src3c.pk024.m11 (SEQ ID NO:4), sah1c.pk002.n23 (SEQ ID NO:6), wheat clone wdk1c.pk010.o10 (SEQ ID NO:8) and the β-amyrin synthases from *Panax ginseng* (NCBI General Identifier No. 3721856; SEQ ID NO:12, and NCBI General Identifier No. 3688600; SEQ ID NO:13). The top row indicates with asterisks (*) the amino acids conserved among all sequences. Dashes are used by the program to maximize the alignment of the sequences.

SEQ ID NO:1 is the nucleotide sequence comprising the soybean cDNA insert in clone sdp3c.pk020.o10 encoding a soybean oxidosqualene cyclase.

SEQ ID NO:2 is the deduced amino acid sequence of a soybean oxidosqualene cyclase derived from the nucleotide sequence of SEQ ID NO:1.

SEQ ID NO:3 is the nucleotide sequence comprising the soybean cDNA insert in clone src3c.pk024.m11 encoding a soybean β-amyrin synthase.

SEQ ID NO:4 is the deduced amino acid sequence of a soybean β-amyrin synthase derived from the nucleotide sequence of SEQ ID NO:3.

SEQ ID NO:5 is the nucleotide sequence comprising the soybean cDNA insert in clone sah1c.pk002.n23 encoding a soybean oxidosqualene cyclase.

SEQ ID NO:6 is the deduced amino acid sequence of a soybean oxidosqualene cyclase derived from the nucleotide sequence of SEQ ID NO:5.

SEQ ID NO:7 is the nucleotide sequence comprising the wheat cDNA insert in clone wdk1c.pk010.o10 encoding a wheat oxidosqualene cyclase.

SEQ ID NO:8 is the deduced amino acid sequence of a wheat oxidosqualene cyclase derived from the nucleotide sequence of SEQ ID NO:7.

SEQ ID NO:9 is the nucleotide sequence of an oligonucleotide primer used to amplify the cDNA insert from clone src3c.pk0024.m11.

SEQ ID NO:10 is the nucleotide sequence of an oligonucleotide primer used to amplify the cDNA insert from clone sah1c.pk002.n23.

SEQ ID NO:11 is the nucleotide sequence of an oligonucleotide primer used for PCR amplification of oxidosqualene cyclase sequences from clones src3c.pk0024.m11 and sah1c.pk002.n23.

SEQ ID NO:12 is the amino acid sequence of a *Panax ginseng* β-amyrin synthase having NCBI General Identifier No. 3721856.

SEQ ID NO:13 is the amino acid sequence of a *Panax ginseng* β-amyrin synthase having NCBI General Identifier No. 3688600.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide/isolated polynucleotide" and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA or mixtures thereof. An isolated polynucleotide of the present invention may include at least 60 contiguous nucleotides, preferably at least 40 contiguous nucleotides, most preferably at least 30 contiguous nucleotides derived from a nucleotide sequence selected from the group consisting of SEQ ID NOs:1, 3, 5, and 7, or the complement of such sequences.

The term "isolated" polynucleotide is one that has been substantially separated or purified away from other nucleic acid sequences in the cell of the organism in which the nucleic acid naturally occurs, i.e., other chromosomal and extrachromosomal DNA and RNA, by conventional nucleic acid purification methods. The term also embraces recombinant polynucleotides and chemically synthesized polynucleotides.

The present invention is directed to isolated polynucleotides and chimeric genes encoding oxidosqualene cyclase enzymes. While not intending to be bound by any theory or theories of operation, it is believed that these enzymes are membrane bound. Oxidosqualene cyclases include and are not limited to β-amyrin synthase, squalene monooxygenase, cycloartenol synthase and the like. Triterpene synthesis is catalyzed by oxidosqualene cyclases. Triterpenes, also known as triterpenoids, include and are not limited to sapinogenins and sterols. The sapinogenin, β-amyrin, is produced by the action of β-amyrin synthase on 2,3-oxidosqualene, for example.

As used herein, "substantially similar" refers to nucleic acid sequences wherein changes in one or more nucleotide bases results in substitution of one or more amino acids, that do not affect the functional properties of the polypeptide encoded by the nucleic acid sequence. "Substantially similar" also refers to polynucleotides wherein changes in one or more nucleotide bases does not affect the ability of the nucleic acid sequence to mediate alteration of gene expression by antisense or co-suppression technology among others. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting polpeptide. It is therefore understood that the invention encompasses more than the specific exemplary sequences.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid sequence which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, and 7 and the complement of such nucleotide sequences may be used in methods of selecting an isolated polynucleotide that affects the expression of an oxidosqualene cyclase polypeptide in a host cell. A method of selecting an isolated polynucleotide that affects the level of expression of an oxidosqualene cyclase polypeptide in a host cell (eukaryotic, such as plant or yeast for example, or prokaryotic, such as bacterial for example) or virus may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al., (1993) J. Mol. Biol. 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequence encoding the oxidosqualene cyclase proteins as set forth in SEQ ID NOs:2, 4, 6, and 8. The skilled artisan is well aware of the "codon-bias" exhibited by a specific host cell in usage of nucleotide codons to specify a given amino acid. Therefore, when synthesizing a polynucleotide for improved expression of a specific gene in a host cell, it is desirable to design the polynucleotide such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences upstream (5' non-coding sequences), within, and downstream (3' non-coding sequences) the coding sequence. "Native gene" refers to a gene as found in nature with its own regulatory sequences. "Chimeric or heterologous" "gene or polynucleotide" refers any gene or polynucleotide that is not native to a plant. A chimeric or heterologous gene comprises regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a polynucleotide sequence capable of controlling the expression of a coding sequence or functional RNA. In general, a coding sequence is located 3' to a promoter sequence. The promoter sequence consists of proximal and more distal upstream elements; the latter elements often referred to as enhancers. Accordingly, an "enhancer" is a nucleotide sequence, which can stimulate promoter activity, and may be an inmate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a DNA that is complementary to and derived from an mRNA. The cDNA can be single-stranded or converted into the double stranded form using, for example, the klenow fragment of DNA polymerase I. "Sense" RNA refers to RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "recombinant" means, for example, that a recombinant nucleic acid sequence is made by an artificial combination of two otherwise separated segments of sequence, e.g., by chemical synthesis or by the manipulation of isolated segments of nucleic acids by genetic engineering techniques.

The term "expression", as used herein refers to the transcription and stable accumulation of sense (mRNA) or antisense RNA derived from a polynucleotide of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" or "altered expression" refers to the production of gene product(s) in transgenic organisms in amounts or proportions that differ from that of normal or non-transformed organisms.

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be but are not limited to intracellular localization signals.

A "signal peptide" is an amino acid sequence which is translated in conjunction with a protein and directs the protein to the secretory system (Chrispeels (1991) *Ann. Rev. Plant Phys. Plant Mol. Biol*. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys*. 100:1627–1632). A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol*. 143:277) and particle-accelerated or "gene gun" transformation technology (Klein et al. (1987) *Nature (London)* 327:70–73; U.S. Pat. No. 4,945,050, incorporated herein by reference).

Expression of a chimeric oxidosqualene cyclase, for example, results in the production of a level of the encoded oxidosqualene cyclase protein in a transformed host cell that is altered as compared to the level produced in an untransformed host cell. Also, a transgenic plant, or plant part, comprising a polynucleotide of the present invention, such as for example, SEQ ID NOS:1, 3, 5, and 7, under the control of a heterologous promoter results in plants having altered levels of triterpenes. Plants may be selected from the group consisting of monocots and dicots. Monocots include and are not limted to corn, rice, wheat, barley, palm, and the like. Dicots include and are not limited to Arabidopsis, soybean, oilseed Brassica, peanut, sunflower, safflower, cotton, tobacco, tomato, potato, cocoa, and the like. Plant parts include and are not limited to seeds and grains, for example.

Thus, isolated polynucleotides of the present invention can be incorporated into recombinant constructs capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Sambrook").

"PCR" or "polymerase chain reaction" is a technique for the synthesis of large quantities of specific DNA segments. It consists of a series of repetitive cycles (Perkin Elmer Cetus Instruements, Norwark, Conn.). Typically, the double-stranded DNA is heat denatured, the two primers complementary to the 3' boundaries of the target segments are annealed at low temperature and then extended at an intermediate temperature. One set of these three consecutive steps is referred to as a cycle.

Nucleic acid fragments encoding oxidosqualene cyclases have been isolated and identified by comparison of random plant cDNA sequences to public databases containing nucleotide and protein sequences using the BLAST algorithms well known to those skilled in the art. Furthermore, their expression has been functionally demonstrated in yeast. Included herein are nucleotide and amino acid sequences with similarities to oxidosqualene cyclase. β-amyrin synthase converts 2,3-oxidosqualene to β-amyrin, which is a required step in the synthesis of saponins in soybean seeds. Elimination of saponins may therefore lead to improved flavor.

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other oxidosqualene cyclases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Sambrook). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full-length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) Proc. Natl. Acad. Sci. USA 86:5673–5677; Loh et al., (1989) Science 243:217–220). Products generated by the 3' and 5' RACE procedures can be combined to generate full-length cDNAs (Frohman and Martin (1989) Techniques 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) Adv. Immunol. 36:1–34; Sambrook).

The nucleic acid fragments of the instant invention may be used to create transgenic plants in which the disclosed oxidosqualene cyclase is present at higher or lower levels than normal or in cell types or developmental stages in which it is not normally found. This would have the effect of altering the relative sterol composition in those cells. These changes in the plant seed may be useful to improve the seed nutritional value, and in the plant leaf may aid in insect tolerance.

Overexpression of oxidosqualene cyclase proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) EMBO J. 4:2411–2418; De Almeida et al., (1989) Mol. Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptide to different cellular compartments, or to facilitate its secretion from the cell. It is thus envisioned that the chimeric gene described above may be further supplemented by altering the coding sequence to encode a triterpenoid with appropriate intracellular targeting sequences such as transit sequences (Keegstra (1989) Cell 56:247–253), signal sequences or sequences encoding endoplasmic reticulum localization (Chrispeels (1991) Ann. Rev. Plant Phys. Plant Mol. Biol. 42:21–53), or nuclear localization signals (Raikhel (1992) Plant Phys. 100:1627–1632) with or without removing targeting sequences that are already present. While the references cited give examples of each of these, the list is not exhaustive and more targeting signals of utility may be discovered in the future.

It may also be desirable to reduce or eliminate expression of genes encoding oxidosqualene cyclase in plants for some applications. In order to accomplish this, a chimeric gene designed for co-suppression of the instant enzymes can be constructed by linking a gene or gene fragment encoding an oxidosqualene cyclase to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant oxidosqualene cyclase (or portions thereof) may be produced in heterologous host cells, particularly in the cells of microbial hosts, and can be used to prepare antibodies to these proteins by methods well known to those skilled in the art. The antibodies are useful for detecting oxidosqualene cyclase in situ in cells or in vitro in cell extracts. Preferred heterologous host cells for production of the instant oxidosqualene cyclase are microbial hosts. Microbial expression systems and expression vectors containing regulatory sequences that direct high level expression of foreign proteins are well known to those skilled in the art. Any of these could be used to construct a chimeric gene for production of the instant oxidosqualene cyclase. This chimeric gene could then be introduced into appropriate microorganisms via transformation to provide high level expression of the encoded enzymes involved in squalene metabolism. An example of a vector for high level expression of the instant oxidosqualene cyclase in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Sambrook) of restriction-digested plant genomic DNA may be probed with the nucleic acid fragments of the instant invention. The resulting banding patterns may then be subjected to genetic analyses using computer programs such as MapMaker (Lander et al., (1987) Genomics 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al., (1980) Am. J. Hum. Genet. 32:314–331).

The production and use of plant gene-derived probes for use in genetic mapping is described in Bernatzky and Tanksley (1986) Plant Mol. Biol. Reporter 4(1):37–41. Numerous publications describe genetic mapping of specific cDNA clones using the methodology outlined above or variations thereof For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet*. 7:149–154). Although current methods of FISH mapping favor use of large clones (several to several hundred KB; see Laan et al. (1995) *Genome Res*. 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med*. 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res*. 18:3671), Radiation Hybrid Mapping (Walter et al. (1997) *Nat. Genet*. 7:22–28) and Happy Mapping (Dear and Cook (1989) *Nucleic Acid Res*. 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci. USA* 86:9402–9406; Koes et al. (1995) *Proc. Natl. Acad. Sci. USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the oxidosqualene cyclase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding an oxidosqualene cyclase can be identified and obtained. This mutant plant can then be used to determine or confirm the natural function of the oxidosqualene cyclase gene product.

While not intending to be bound by any theory or theories of operation, it is believed by those of skill in the art that altered levels of triterpenes have different effects. Foods originating from plants having an increased level of triterpenes are thought to have a cholesterol lowering effect while decreased triterpenes are believed to result in better tasting foods. Accordingly, plants grown with altered levels of oxidosqualene cyclases may contribute to nutritious and/or better flavored foods.

In another embodiment, the present invention is directed to a variety of plant or vegetable protein products. A variety of processed vegetable protein products are produced from soybean. These are useful in and as food products including and not limited to human foods as well as animal feed products. These range from minimally processed, soy beans and soy nuts such as toasted soy nuts, defatted items such as soybean meal, grits, and flours to more highly processed items such as soy protein concentrates and soy protein isolates. In other soy protein products, such as full-fat soy flour, the oil is not extracted. In addition to these processed products, there are also a number of specialty products based on traditional Oriental processes, which utilize the entire bean as the starting material, also known as the "whole bean method." Examples of additional products include milk (liquid and powder) including and not limited to soy milk, soy sauce, nuts including soy nuts, tofu, natto, miso, tempeh, and yuba.

Examples of use of soy protein products in human foods include soy milk, applying soy protein concentrates and soy protein isolates in nutritional beverage, emulsified meat and whole muscle meat applications, textured soy protein in meat analogue, and soy protein isolate in infant formula. Facilities and methods to produce protein concentrates and isolates from soybeans are available across the world. To the extent that they are retained in these processed soy fractions and the foods prepared from them, the saponin content of the starting beans influences the flavor of the food.

The present invention is further defined in the following Examples, in which all parts and percentages are by weight and degrees are Celsius, unless otherwise stated. Examples 1–4 are actual, Examples 5–7 are prophetic. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated by reference in its entirety.

EXAMPLES

Example 1

Composition of cDNA Libraries; Isolation and Sequencing of cDNA Clones cDNA libraries representing mRNAs from various soybean and wheat tissues were prepared. The characteristics of the libraries are described below.

TABLE 2 cDNA Libraries from Soybean and Wheat

| Library | Tissue | Clone |
|---|---|---|
| sdp3c | Soybean (Glycine max L.) developing pods 8–9 mm | sdp3c.pk020.o10 |
| src3c | Soybean (Glycine max L., Bell) 8 day old root inoculated with eggs of Cyst Nematode (Race 14) for 4 days | src3c.pk024.m11 |
| sah1c | Soybean (Glycine max L., 9151) sprayed with Authority Herbicide | sah1c.pk002.n23 |
| wdk1c | Wheat (Triticum aestivum L.) developing kernel, 3 days after anthesis | wdk1c.pk010.o10 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al. (1991) *Science* 252:1651–1656). The resulting ESTs are analyzed using a Perkin Elmer Model 377 fluorescent sequencer.

Example 2

Identification of cDNA Clones cDNA clones encoding enzymes involved in squalene metabolism were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Oxidosqualene Cyclases

The BLASTX search using the EST sequences from clones sdp3c.pk020.o10, src3c.pk024.m11, sah1c.pk002.n23, wdk1c.pk010.o10 revealed similarity of the proteins encoded by the cDNAs to β-amyrin synthases from *Panax ginseng* (NCBI General Identifier Nos. 3721856 and 3688600) and to the proteins encoded by the contig to cycloartenol synthase from *Arabidopsis thaliana* (NCBI General Identifier No. 3779033). The BLAST results for each of these ESTs are shown in Table 3:

TABLE 3

BLAST Results for Clones Encoding Polypeptides Homologous to β-amyrin synthase

| Clone | NCBI General Identifier No. | BLAST pLog Score |
|---|---|---|
| sdp3c.pk020.o10 | 3688600 | 0.02 |
| src3c.pk024.m11 | 3721856 | 12.77 |
| sah1c.pk002.n23 | 3721856 | 6.09 |
| wdk1c.pk010.o10 | 3779033 | 18.96 |

A 550 base pair soybean EST having NCBI General Identifier No. 5606831 has been identified as "similar to β-amyrin synthase," according to the NCBI entrez. Based on Clustal alignment, this sequence is 62.0% identical to SEQ ID NO:1, 62.9% to SEQ ID NO:3, 64.2% to SEQ ID NO:5, and 38.4% to SEQ ID NO:7. The longest contiguous stretch of identity is 18 nucleotides. This 18 nucleotide stretch corresponds to nucleotides 2372 through 2390 from sah1c.pk002.n23 and nucleotides 120 through 138 from NCBI General Identifier No. 5606831.

The sequence of the entire cDNA insert from clone sdp3c.pk020.o10 is shown in SEQ ID NO:1; the deduced amino acid sequence of this cDNA is shown in SEQ ID NO:2. The sequence of the entire cDNA insert from clone src3c.pk024.m11 is shown in SEQ ID NO:3; the deduced amino acid sequence of this cDNA is shown in SEQ ID NO:4. The sequence of the entire cDNA insert from clone sah1c.pk002.n23 is shown in SEQ ID NO:5; the deduced amino acid sequence of this cDNA is shown in SEQ ID NO:6. The sequence of the entire cDNA insert from clone wdk1c.pk010.o10 is shown in SEQ ID NO:7; the deduced amino acid sequence of this cDNA is shown in SEQ ID NO:8.

FIG. 1 A–E presents an alignment of the amino acid sequences set forth in SEQ ID NOs:2, 4, 6, and 8 and the *Panax ginseng* sequences (SEQ ID NO:12; NCBI General Identifier No. 3721856, and SEQ ID NO:13; NCBI General Identifier No. 3688600). The data in Table 4 represents a calculation of the percent identity of the amino acid sequences set forth in SEQ ID NOs:2, 4 6, and 8 and the *Panax ginseng* sequences (SEQ ID NOs:12 and 13).

TABLE 4

Percent Identity of Amino Acid Sequences Deduced From the Nucleotide Sequences of cDNA Clones Encoding Polypeptides Homologous to β-amyrin synthase

| SEQ ID NO. | Percent Identity to | |
|---|---|---|
| | 3721856 | 3688600 |
| 2 | 75.2 | 76.2 |
| 4 | 78.4 | 79.0 |
| 6 | 71.1 | 70.9 |
| 8 | 51.2 | 50.9 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode entire or almost entire soybean and wheat oxidosqualene cyclases. These sequences are among the first monocot and soybean sequences known to encode oxidosqualene cyclases.

Example 4

Demonstration of Functional Expression of β-amyrin Synthase in Yeast

The inserts in cDNA clones src3c.pk024.m11 and sah1c.pk002.n23 were identified as candidate β-amyrin synthase genes by a BLAST search against the NCBI database. The 5' sequence of these inserts was determined to be related to either of the β-amyrin synthases from *Panax ginseng*, the complete coding sequence of which may be found as DDBJ Accession Nos. AB014057 and AB009030 having NCBI General Identifier Nos. 3721856 and 3688600. β-amyrin synthase catalyzes the cyclization of 2,3-oxidosqualene to β-amyrin. In order to confirm the identity of the polypeptides encoded by the inserts in cDNA clones src3c.pk024.m11 and sah1c.pk002.n23 as β-amyrin synthase, the polypeptides encoded by these inserts were evaluated for their ability to catalyze the formation of β-amyrin.

The ability of the cDNA inserts in clones src3c.pk024.m11 and sah1c.pk002.n23 to encode β-amyrin synthase was evaluated by expression of the encoded polypeptides in a yeast (*Saccharomyces cerivisae*) strain YPH (Stratagene) and examining the membrane components. Plasmid DNA (200 ng) from cDNA clone src3c.pk024.m11 was used as template for PCR using primers set forth in SEQ ID NO:9 and SEQ ID NO:11. Plasmid DNA (200 ng) from cDNA clone sah1c.pk002.n23 was used as template for PCR using primers set forth in SEQ ID NO:10 and SEQ ID NO:11. The 24 nucleotides at the 5' terminus of both primers set forth as SEQ ID NO:9 and SEQ ID NO:10 are homologous to the modified pRS315 plasmid described below. The 22 nucleotides at the 3' terminus of the primer set forth in SEQ ID NO:9 is derived from the start of transcription of the protein encoded by clone src3c.pk0024.m11. The 22 nucleotides at the 3' terminus of the primer set forth in SEQ ID NO:10 is derived from the start of transcription of the protein encoded by clone sah1c.pk002.n23. The sequence of the primer set forth as SEQ ID NO:11 is homologous to vector sequences.

```
5'-TCAAGGAGAAAAAACCCCGGATCCATGTGGAGGCTGAAGATAGCAG-3'    [SEQ ID NO:9]

5'-TCAAGGAGAAAAAACCCCGGATCCATGTGGAGGTTAAAGATAGCAG-3'    [SEQ ID NO:10]

5'-GGCCAGTGAATTGTAATACGACTCACTATAGGGCG-3'               [SEQ ID NO:11]
```

Amplification was performed using the GC melt kit (Clontech) with a 1 M final concentration of GC melt reagent. Amplification took place in a Perkin Elmer 9700 thermocycler for 30 cycles as follows: 94° C. for 30 seconds, 60° C. for 30 seconds, and 72° C. for 2 minutes. The amplified insert was then incubated with a modified pRS315 plasmid (NCBI General Identifier No. 984798; Sikorski, R. S. and Hieter, P. (1989) *Genetics* 122:19–27) that had been digested with Not I and Spe I. Plasmid pRS315 had been previously modified by the insertion of a bidirectional gal1/10 promoter between the Xho I and Hind III sites. The plasmid was then transformed into the YPH yeast strain using standard procedures where the insert recombines through gap repair to form the desired transformed yeast strain (Hua, S. B. et al. (1997) *Plasmid* 38:91–96.). The resulting transformed yeast strains were named Yeast Strains β-amyrin X and β-amyrin Y.

Yeast cells were prepared according to a modification of the methods of Pompon et al. (Pompon, D. et al. (1996) *Meth. Enz.* 272:51–64). Briefly, a yeast colony was grown overnight (to saturation) in SG (-Leucine) medium at 30° C. with good aeration. A 1:50 dilution of this culture was made into 500 mL of YPGE medium with adenine supplementation and allowed to grow at 30° C. with good aeration to an $OD_{600}$ of 1.6 (24–30 h). Fifty mL of 20% galactose was added, and the culture was allowed to grow overnight at 30° C. The cells were recovered by centrifugation at 5,500 rpm for five minutes in a Sorvall GS-3 rotor. The cell pellet was resuspended in 500 mL of 0.1 M potassium phosphate buffer (pH 7.0) and then allow to grow at 30° C. for another 24 hours.

The cells were recovered by centrifugation as described above and the presence of β-amyrin was determined by HPLC/mass spectrometry.

The cDNA insert in clones src3c.pk024.m11 and sah1c.pk002.n23 resulted in decectable levels of β-amyrin. The results were not repeatable using the cDNA insert in clone sah1c.pk002.n23. This example was repeated in a different yeast background (overexpressing HMG-CoA reductase) using the cDNA inserts from clones src3c.pk024.m11, sah1c.pk002.n23, sdp3c.pk020.o10 and wdk1c.pk010.o10. Detectable levels of β-amyrin resulted using the cDNA insert from src3c.pk024.m11.

Example 5

Expression of Chimeric Genes in Monocot Cells

A chimeric gene comprising a cDNA encoding β-amyrin synthase in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Nco I or Sma I) can be incorporated into the oligonucleotides to provide proper orientation of the DNA fragment when inserted into the digested vector pML103 as described below. Amplification is then performed in a standard PCR reaction. The amplified DNA is then digested with restriction enzymes Nco I and Sma I and fractionated on an agarose gel. The appropriate band can be isolated from the gel and combined with a 4.9 kb Nco I-Sma I fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb Sal I-Nco I promoter fragment of the maize 27 kD zein gene and a 0.96 kb Sma I-Sal I fragment from the 3' end of the maize 10 kD zein gene in the vector pGem9Zf(+) (Promega). Vector and insert DNA can be ligated at 15° C. overnight, essentially as described (Sambrook). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U. S. Biochemical). The resulting plasmid construct would comprise a chimeric gene encoding, in the 5' to 3' direction, the maize 27 kD zein promoter, a cDNA encoding β-amyrin synthase, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242,236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) maybe used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains glufosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calluses may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant enzymes β-amyrin synthase in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding β-amyrin synthase. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the enzyme involved in squalene metabolism and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order: 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant enzyme β-amyrin synthase can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 may be constructed by first destroying the EcoR I and Hind III sites in pET-3a at their original positions. An oligonucleotide adaptor containing EcoR I and Hind III sites may be inserted at the BamH I site of pET-3a. This creates pET-3aM with additional unique cloning sites for insertion of genes into the expression vector. Then, the Nde I site at the position of translation initiation is then converted to an Nco I site using oligonucleotide-directed mutagenesis. The DNA sequence of pET-3aM in this region, 5'-CATATGG, is converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the enzyme involved in squalene metabolism may then be screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol*. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

---

What is claimed is:

1. An isolated polynucleotide comprising:
   a) first nucleotide sequence encoding a polypeptide having β-amyrin synthase [oxidosqualene cyclase] activity, wherein the polypeptide has an amino acid sequence of at least 80% sequence identity based on the Clustal method of alignment when compared to a polypeptide of SEQ ID: 4; wherein the default parameters for pairwise alignment are KTUPLE=1, GAP PENALTY=3, WINDOW=5 and DIAGONALS SAVED=5; and
   b) a full complement of the nucleotide sequence of a).

2. The isolated polynucleotide of claim 1 wherein the nucleotide sequences are DNA.

3. The isolated polynucleotide of claim 1 wherein the nucleotide sequences are RNA.

4. A chimeric polynucleotide comprising the isolated polynucleotide of claim 1 operably linked to a suitable regulatory sequence.

5. An isolated host cell comprising the chimeric polynucleotide of claim 4.

6. An isolated host cell comprising the polynucleotide of claim 1.

7. The host cell of claim 6 wherein said host cell is selected from the group consisting of a yeast cell, a bacterial cell, and a plant cell.

8. A plant comprising the chimeric polynucleotide of claim 4.

9. A transgenic plant comprising a polynucleotide of claim 1 under the control of a heterologous promoter, said plant having an altered level of a triterpene.

10. The plant of claim 9 wherein said triterpene is a saponin derived from β-amyrin and said level is increased.

11. The plant of claim 9 wherein said triterpene is a saponin derived from β-amyrin and said level is decreased.

12. The plant of claim 9 wherein said plant is selected from the group consisting of a monocot and a dicot.

13. The plant of claim 12 wherein said monocot is selected from the group consisting of corn, rice, wheat, barley, and palm.

14. The plant of claim 12 wherein said dicot is selected from the group consisting of *Arabidopsis*, soybean, oilseed *Brassica*, peanut, sunflower, safflower, cotton, tobacco, tomato, potato, and cocoa.

15. A method of altering the level of expression of a β-amyrin synthase [an oxidosqualene cyclase] polypeptide in a plant cell, which comprises:
   a) constructing an isolated polynucleotide comprising a nucleotide sequence of at least 30 contiguous nucleotides obtained from an isolated polynucleotide of claim 1;
   b) introducing the isolated polynucleotide into a plant cell;
   c) growing the plant cell of b) under conditions suitable for expression of the recombinant polynucleotide;
   d) measuring the level of β-amyrin synthase [oxidosqualene cyclase] in the plant cell containing the polynucleotide; and
   e) comparing the level of β-amyrin synthase [oxidosqualene cyclase] in the plant cell containing the recombinant polynucleotide with the level of β-amyrin synthase [oxidosqualene cyclase] in a plant cell of the same species as the plant cell of step b) that does not contain the recombinant polynucleotide.
   wherein the plant cell containing the recombinant polynucleotide produces an amount of β-amyrin synthase [oxidosqualene cyclase] that is altered when compared to the amount of β-amyrin synthase [oxidosqualene cyclase] produced by the plant cell not containing the recombinant polynucleotide.

16. A method of producing a plant with altered levels of β-amyrin synthase comprising:
   a) transforming a plant cell with the chimeric polynucleotide of claim 4;
   b) growing the transformed plant cell from step (a) under conditions that are suitable for expression of the chimeric polynucleotide and that promote the regeneration of a whole plant from the transformed cell;
   wherein the plant regenerated from the transformed cell produces an amount of β-amyrin synthase that is greater or lower than the amount of the β-amyrin synthase that is produced in a plant that is regenerated from a plant cell of the same species as the plant of step (a) that is not transformed with the chimeric polynucleotide of claim 4; and optionally
   c) transforming the plant cell of step (a) with a second chimeric polynucleotide comprising a nucleic acid sequence encoding a polypeptide that regulates expression of at least one enzyme of the triterpene pathway; and
   d) growing the transformed plant cell from step (c) under conditions that are suitable for expression of the second chimeric polynucleotide and that promote the regeneration of a whole plant from the transformed cell; wherein the plant regenerated from the transformed cell produces an amount of β-amyrin synthase that is greater or lower than the amount of the β-amyrin synthase that is produced in a plant that is regenerated from a plant cell of the same species as the plant of step (c) that is not transformed with the chimeric polynucleotide of claim 4 and a second chimeric polynucleotide.

17. The polynucleotide of claim 1, wherein the amino acid sequence of the polypeptide has at least 85% sequence identity, based on the said Clustal method of alignment, when compared to SEQ ID NO: 4.

18. The polynucleotide of claim 1, wherein the amino acid sequence of the polypeptide has at least 90% sequence identity, based on the said Clustal method of alignment, when compared to SEQ ID NO:4.

19. The polynucleotide of claim 1, wherein the amino acid sequence of the polypeptide has at least 95% sequence identity, based on the said Clustal method of alignment, when compared to SEQ ID NO:4.

20. The polynucleotide of claim 1, wherein the amino acid sequence of the polypeptide comprises SEQ ID NO:4.

21. The polynucleotide of claim 1 wherein the nucleotide sequence comprises SEQ ID NO: 3.

* * * * *

SEQUENCE LISTING

<160> NUMBER OF SEQ ID NOS: 13

<210> SEQ ID NO 1
<211> LENGTH: 2731
<212> TYPE: DNA
<213> ORGANISM: Glycine max

<400> SEQUENCE: 1

```
atagattcga ggacagattt taaaagcaac ctaagttttg tatttacaaa actgagcttc      60
cagaaggaaa aaaaaaatca atttgctaaa gttattttag gataactaac taagcatgtc     120
aagaaatcga gtttattctc taaaaatatt ttcaacataa gaaaaacaat acttttttgaa    180 tggttagtaa aacatgtctt taatcagttg cttcgtattt tcatgcagtt aggtgcatca     240
attgactgtg gcattatagc atattaagag aaagcaacaa aatgtggagg ctgaagatag     300
cagatggtgg aaaagaccca tacattttca gcacaaacaa ttttgtagga agacagacat     360
gggagtttga tcctgaggca ggaactccag aggaacgagc tcaagttgaa gcagctcgtc     420 aaaatttttta taacaatcgc ttcaaggtca aggcatgtgg tgatctcctt tggcgttttc    480
agattctgag agaaaaaaac ttcaaacaat caataccttag tgtgaagata aagatggag     540 aagaaataac atacgaaaaa gtcataagca cgttgagaag agccgcacac cacctatcag    600
cattgcagac cagtgatggc cattggcctg cacaaattgc aggtcctctg ttttttctgc    660
ctcctttggt ttttttgtatg tacattacag ggcatcttga tttggtattc ccagaagagt    720
atcgaaaaga gattctccgt tacatatact atcaccagaa tgaagatgga ggatggggac    780
tacacataga gggtcatagc accatgtttg gtactacact aaactatata tgtatgcgaa    840
ttcttggaga agggcctaat ggaggtcatg aaaatgcatg tgctagagga aaaaagtgga    900
ttcatgatca tggtggtgta acacacatcc cttcatgggg gaaaacttgg ctttcgatac    960
ttggtgtatt tgattggtgt ggaagcaacc caatgccccc agagttttgg attattcctt   1020
cgtttcttcc tatgcatcca gctaaaatgt ggtgttattg tcgattggta tatatgccta   1080
tgtcttatat gggaaaaggg tttgtgggtc aatcacacc actcatctta caattgagag    1140
aagagctctt tactcagcct tatgaaaaag ttaattggaa aaaagtgcgt catcaatgtg   1200 caaggaaga tctttattat cctcattctt tgatacaaga cctagtatgg gacagtctat    1260
acatgtttac tgagccacta cttacttgtt ggcctttcaa caaactaatt agagaaaagg   1320
cccttcaagt aacaatgaac catattcatt acgaagatga gaatagtcga tacataacta    1380
ttgggtgtgt ggaaaaggtt ctatgtatgc ttgcttgttg ggttgaagat ccacagggag    1440
atgcctttaa gaagcatctt gcaagggtct cagattactg atgggtttct gaagatggaa    1500
tgaccatgca aagtttttggt agtcaagaat gggatgctgg ttttgcagtt caagctttgc    1560
ttgcaactaa gctaattgac gaaattggcc attcacttgc aaaagggcat gatttcatca    1620
agaagtctca ggtgagagac aacccttcag gagattttaa gagtatgtat cgtcatatta    1680
ctaaagggtc ttggacattc tcagatcaag accatggatg gcaagtttct gattgcactg    1740
```

```
cagaaggttt aaagtgttgt cttcttctat caaagttgtc accagagatt gtgggagaaa    1800
aagtgaaacc tgaaagattt tatgattcag tcaatatctt gttgtcactt cagagtaaaa    1860
aaggtggtat agcagcatgg gaaccaatag gagctcaaga atggttggaa ttactcaatc    1920
ccactgaatt ttttgaggac attgtaattg agcatgaata tgttgagtgc actggatctg    1980
caattcaagc tttagttttg ttccagaagc tatatccaga gcataggaag acagagatta    2040
agaatttcat tgtcaatgca gttcaattcc ttgaagatac acaaacaacc aatggttcat    2100
ggtatggatg ttggggagtt tgctacactt atggctcttg gtttgcactt ggtggtctag    2160
cagctgccgg taagacttac actaattgta atgccattcg caaggctgtg aaatttctac    2220
ttacaacaca gagagaggat ggtgggtggg gagagagtta tctttcaagc ccaaaaaaga    2280
tatacatacc tcttgaagga agtcgatcaa acgttgtaca acagcatgg gctcttatgg    2340 gtctaattta tgctggacag tcagagagag accttactcc tcttcatcga gctgcaaagt    2400
tgctcattaa ttcccagttg gaagaaggtg attggcccca acaggaaatc actggagtat    2460
tcttgaaaaa ctgcatgatg cattacccaa tgtatagaaa tattttttcca atgtgggctc    2520 tagctgaata tcgtaggcga gttccattgc catccactga aggttaattt tgaaaaggtg    2580
tgtgcataaa agggcaaaga catatcaatg aggaatgggg caagaagcac ccattgtctc    2640
ttacttggac tctattgatc tgtaattttg aagcttgctt tttattataa aataaaaaat    2700
tatttacgca caaaaaaaaa aaaaaaaaaa a                                   2731

<210> SEQ ID NO 2
<211> LENGTH: 761
<212> TYPE: PRT
<213> ORGANISM: Glycine max

<400> SEQUENCE: 2

Met Trp Arg Leu Lys Ile Ala Asp Gly Gly Lys Asp Pro Tyr Ile Phe
  1               5                  10                  15

Ser Thr Asn Asn Phe Val Gly Arg Gln Thr Trp Glu Phe Asp Pro Glu
                 20                  25                  30

Ala Gly Thr Pro Glu Glu Arg Ala Gln Val Glu Ala Ala Arg Gln Asn
             35                  40                  45

Phe Tyr Asn Asn Arg Phe Lys Val Lys Ala Cys Gly Asp Leu Leu Trp
         50                  55                  60

Arg Phe Gln Ile Leu Arg Glu Lys Asn Phe Lys Gln Ser Ile Pro Ser
 65                  70                  75                  80

Val Lys Ile Glu Asp Gly Glu Glu Ile Thr Tyr Glu Lys Val Ile Ser
                 85                  90                  95

Thr Leu Arg Arg Ala Ala His His Leu Ser Ala Leu Gln Thr Ser Asp
            100                 105                 110

Gly His Trp Pro Ala Gln Ile Ala Gly Pro Leu Phe Phe Leu Pro Pro
        115                 120                 125

Leu Val Phe Cys Met Tyr Ile Thr Gly His Leu Asp Leu Val Phe Pro
    130                 135                 140

Glu Glu Tyr Arg Lys Glu Ile Leu Arg Tyr Ile Tyr His Gln Asn
145                 150                 155                 160

Glu Asp Gly Gly Trp Gly Leu His Ile Glu Gly His Ser Thr Met Phe
                165                 170                 175

Gly Thr Thr Leu Asn Tyr Ile Cys Met Arg Ile Leu Gly Glu Gly Pro
            180                 185                 190
```

```
Asn Gly Gly His Glu Asn Ala Cys Ala Arg Gly Lys Lys Trp Ile His
        195                 200                 205

Asp His Gly Gly Val Thr His Ile Pro Ser Trp Gly Lys Thr Trp Leu
    210                 215                 220

Ser Ile Leu Gly Val Phe Asp Trp Cys Gly Ser Asn Pro Met Pro Pro
225                 230                 235                 240

Glu Phe Trp Ile Ile Pro Ser Phe Leu Pro Met His Pro Ala Lys Met
                245                 250                 255

Trp Cys Tyr Cys Arg Leu Val Tyr Met Pro Met Ser Tyr Met Gly Lys
            260                 265                 270

Gly Phe Val Gly Pro Ile Thr Pro Leu Ile Leu Gln Leu Arg Glu Glu
        275                 280                 285

Leu Phe Thr Gln Pro Tyr Glu Lys Val Asn Trp Lys Lys Val Arg His
    290                 295                 300

Gln Cys Ala Lys Glu Asp Leu Tyr Tyr Pro His Ser Leu Ile Gln Asp
305                 310                 315                 320

Leu Val Trp Asp Ser Leu Tyr Met Phe Thr Glu Pro Leu Leu Thr Cys
                325                 330                 335

Trp Pro Phe Asn Lys Leu Ile Arg Glu Lys Ala Leu Gln Val Thr Met
            340                 345                 350

Asn His Ile His Tyr Glu Asp Glu Asn Ser Arg Tyr Ile Thr Ile Gly
        355                 360                 365

Cys Val Glu Lys Val Leu Cys Met Leu Ala Cys Trp Val Glu Asp Pro
    370                 375                 380

Gln Gly Asp Ala Phe Lys Lys His Leu Ala Arg Val Ser Asp Tyr Leu
385                 390                 395                 400

Trp Val Ser Glu Asp Gly Met Thr Met Gln Ser Phe Gly Ser Gln Glu
                405                 410                 415

Trp Asp Ala Gly Phe Ala Val Gln Ala Leu Leu Ala Thr Lys Leu Ile
            420                 425                 430

Asp Glu Ile Gly His Ser Leu Ala Lys Gly His Asp Phe Ile Lys Lys
        435                 440                 445

Ser Gln Val Arg Asp Asn Pro Ser Gly Asp Phe Lys Ser Met Tyr Arg
    450                 455                 460

His Ile Thr Lys Gly Ser Trp Thr Phe Ser Asp Gln Asp His Gly Trp
465                 470                 475                 480

Gln Val Ser Asp Cys Thr Ala Glu Gly Leu Lys Cys Cys Leu Leu Leu
                485                 490                 495

Ser Lys Leu Ser Pro Glu Ile Val Gly Glu Lys Val Lys Pro Glu Arg
            500                 505                 510

Phe Tyr Asp Ser Val Asn Ile Leu Leu Ser Leu Gln Ser Lys Lys Gly
        515                 520                 525

Gly Ile Ala Ala Trp Glu Pro Ile Gly Ala Gln Glu Trp Leu Glu Leu
    530                 535                 540

Leu Asn Pro Thr Glu Phe Phe Glu Asp Ile Val Ile Glu His Glu Tyr
545                 550                 555                 560

Val Glu Cys Thr Gly Ser Ala Ile Gln Ala Leu Val Leu Phe Gln Lys
                565                 570                 575

Leu Tyr Pro Glu His Arg Lys Thr Glu Ile Lys Asn Phe Ile Val Asn
            580                 585                 590

Ala Val Gln Phe Leu Glu Asp Thr Gln Thr Thr Asn Gly Ser Trp Tyr
        595                 600                 605

Gly Cys Trp Gly Val Cys Tyr Thr Tyr Gly Ser Trp Phe Ala Leu Gly
```

-continued

```
          610                 615                 620
Gly Leu Ala Ala Ala Gly Lys Thr Tyr Thr Asn Cys Asn Ala Ile Arg
625                 630                 635                 640

Lys Ala Val Lys Phe Leu Leu Thr Thr Gln Arg Glu Asp Gly Gly Trp
                645                 650                 655

Gly Glu Ser Tyr Leu Ser Ser Pro Lys Lys Ile Tyr Ile Pro Leu Glu
            660                 665                 670

Gly Ser Arg Ser Asn Val Val Gln Thr Ala Trp Ala Leu Met Gly Leu
        675                 680                 685

Ile Tyr Ala Gly Gln Ser Glu Arg Asp Leu Thr Pro Leu His Arg Ala
690                 695                 700

Ala Lys Leu Leu Ile Asn Ser Gln Leu Glu Glu Gly Asp Trp Pro Gln
705                 710                 715                 720

Gln Glu Ile Thr Gly Val Phe Leu Lys Asn Cys Met Met His Tyr Pro
                725                 730                 735

Met Tyr Arg Asn Ile Phe Pro Met Trp Ala Leu Ala Glu Tyr Arg Arg
                740                 745                 750

Arg Val Pro Leu Pro Ser Thr Glu Gly
        755                 760
```

<210> SEQ ID NO 3
<211> LENGTH: 2478
<212> TYPE: DNA
<213> ORGANISM: Glycine max

<400> SEQUENCE: 3

```
ggtttgtttg gtgtgagtga atagggatca gggatgtgga ggctgaagat agcagatgga    60
ggaaatgatc catacatatt cagcacaaac aatttcgttg ggaggcagac atgggagttt   120
gatcctgaag caggcagtcc agaggaacgg gcccaggttg aagcagctcg tcagcatttc   180
taccacaacc gcttcaaggt caagccctgc gctgacctcc tttggcgttt tcaggttctc   240
agagaaaata acttcaaaca acaattcct cgtgtgacta gaagatgg agaggaaatc      300
acataccaaa aagtcacaag cgccgtcaga aggggcgcac accaccttgc ggcactgcag   360
acctctgatg gccattggcc tgctcaaatt gcaggtcctc tcttctttct tcctcccttg   420
gttttttgta tgtatattac aggaaatctt gaatcagtat ttccagaaga acatcgcaaa   480
gaaattcttc gttacacata ttatcaccag aatgaagacg gaggatgggg actacacata   540
gagggtcata gcactatgtt tgtactgca ctgaactata tgcatgcg aatgcttgga      600
gaaggaccta atggaggtca tgacaatgct tgtgctagag caagaaagtg gattcgagat   660
catggtggtg taacacatat accttcatgg ggaaaaactt ggctttcgat actcggtgta   720
tttgattggt gcggaagcaa cccaatgccc ccagagtttt ggatccttcc atctttctct   780
cctatgcatc cagctaagat gtggtgttac tgtcgattgg tatacatgcc tatgtcttac   840
ttatatggga agaggtttgt gggtccaatc acaccactca tcttacaatt aagagaagag   900
ttgtttactc aacctatga aaagttaat tggaagaaag cgcgtcacca atgtgcaaag     960
gaagatcttt actatcccca tcctttgata caagacctaa tatgggatag tttatacata  1020
ttcactgaac cgctacttac tcgttggcct ttcaacaagt tgattagaga aaaggccctt  1080
caagtaacta tgaaacatat tcattatgaa gatgagacta gtcgatacat aaccattggt  1140
tgtgtggaaa aggttttatg tatgcttgct tgtggggtgg aagatccaaa cggagatgct  1200
ttcaagaagc atcttgcaag ggtcccagat tacttatggg tttctgaaga tggaatgacc  1260
```

-continued

```
atgcagagtt ttggtagcca agaatgggat gctggctttg ctgttcaagc tttgcttgcc    1320
actaacataa ttgaagaaat tggtcctacg tttgcaaaag acatgatttt catcaagaag    1380
tctcaggtga aggataatcc ttttggagat tttaaaagta tgcatcgtca tatttctaaa    1440
gggtcttgga cattctctga tcaagaccat ggatggcaag tttctgattg cactgcagaa    1500
ggtttaaagt gttgtctact ctatcaatg ttgccaccag agattgtggg agaaaagatg     1560
gaacctgaaa gattatacga ttcagtcaat gtcttgttgt cgcttcagag taaaaaaggt    1620
ggtttagcag catgggagcc tgcaggagct caagagtggt tagaattact caatcccaca    1680 gaatttttg cggacattgt agttgaacat gaatatgttg agtgcactgg atctgcaatc     1740
caagctttag ttttgttcaa gaagctatat ccaggacata ggaagaaaga datagaaaat    1800
ttcattacca atgcagttcg attccttgaa gatacacaaa cagctgatgg ttcatggtat    1860
ggaaattggg gagtttgctt cacttatggc tcttggtttg cacttggagg tctagcagct    1920
gctggtaaga cttacaccaa ttgtgctgcc attcgcaaag ccgttaaatt tctacttaca    1980
acacaaagag aggacggtgg atggggagag agttatcttt caagcccaaa aaagatatat    2040
gtacctctag aaggaagccg atcaaatgtt gtacatacag catgggctct tatgggacta    2100
attcatgctg acaggcgga tagagacccc atgcctcttc accgtgctgc aaagttgctc     2160
attaattctc agttggaaga gggtgattgg ccccaacagg aaatcacggg agtattcatg    2220
aaaaattgca tgttgcatta tccaatgtac agagatattt atccaatgtg ggctctagct    2280
gaatatcgaa ggcgggttcc attgccttcc actgaagttt aatttagaat ggtttgagca    2340
cgaaaaggca aaggcatttt cattaagatt gaggcaaata agttgtgtgt aatcaagctt    2400
aatcaatttt ttcatattcc tatgtttatt tcctacatat attggtagaa aaattatttc    2460
aaaaaaaaaa aaaaaaaa                                                   2478
```

<210> SEQ ID NO 4
<211> LENGTH: 762
<212> TYPE: PRT
<213> ORGANISM: Glycine max

<400> SEQUENCE: 4

```
Met Trp Arg Leu Lys Ile Ala Asp Gly Gly Asn Asp Pro Tyr Ile Phe
  1               5                  10                  15

Ser Thr Asn Asn Phe Val Gly Arg Gln Thr Trp Glu Phe Asp Pro Glu
             20                  25                  30

Ala Gly Ser Pro Glu Glu Arg Ala Gln Val Glu Ala Ala Arg Gln His
         35                  40                  45

Phe Tyr His Asn Arg Phe Lys Val Lys Pro Cys Ala Asp Leu Leu Trp
     50                  55                  60

Arg Phe Gln Val Leu Arg Glu Asn Asn Phe Lys Gln Thr Ile Pro Arg
 65                  70                  75                  80

Val Thr Ile Glu Asp Gly Glu Glu Ile Thr Tyr Gln Lys Val Thr Ser
                 85                  90                  95

Ala Val Arg Arg Gly Ala His His Leu Ala Ala Leu Gln Thr Ser Asp
            100                 105                 110

Gly His Trp Pro Ala Gln Ile Ala Gly Pro Leu Phe Phe Leu Pro Pro
        115                 120                 125

Leu Val Phe Cys Met Tyr Ile Thr Gly Asn Leu Glu Ser Val Phe Pro
    130                 135                 140

Glu Glu His Arg Lys Glu Ile Leu Arg Tyr Thr Tyr Tyr His Gln Asn
145                 150                 155                 160
```

-continued

```
Glu Asp Gly Gly Trp Gly Leu His Ile Glu Gly His Ser Thr Met Phe
            165                 170                 175
Cys Thr Ala Leu Asn Tyr Ile Cys Met Arg Met Leu Gly Glu Gly Pro
            180                 185                 190
Asn Gly Gly His Asp Asn Ala Cys Ala Arg Ala Arg Lys Trp Ile Arg
            195                 200                 205
Asp His Gly Gly Val Thr His Ile Pro Ser Trp Gly Lys Thr Trp Leu
    210                 215                 220
Ser Ile Leu Gly Val Phe Asp Trp Cys Gly Ser Asn Pro Met Pro Pro
225                 230                 235                 240
Glu Phe Trp Ile Leu Pro Ser Phe Leu Pro Met His Pro Ala Lys Met
                245                 250                 255
Trp Cys Tyr Cys Arg Leu Val Tyr Met Pro Met Ser Tyr Leu Tyr Gly
                260                 265                 270
Lys Arg Phe Val Gly Pro Ile Thr Pro Leu Ile Leu Gln Leu Arg Glu
            275                 280                 285
Glu Leu Phe Thr Gln Pro Tyr Glu Lys Val Asn Trp Lys Lys Ala Arg
    290                 295                 300
His Gln Cys Ala Lys Glu Asp Leu Tyr Tyr Pro His Pro Leu Ile Gln
305                 310                 315                 320
Asp Leu Ile Trp Asp Ser Leu Tyr Ile Phe Thr Glu Pro Leu Leu Thr
                325                 330                 335
Arg Trp Pro Phe Asn Lys Leu Ile Arg Glu Lys Ala Leu Gln Val Thr
            340                 345                 350
Met Lys His Ile His Tyr Glu Asp Glu Thr Ser Arg Tyr Ile Thr Ile
            355                 360                 365
Gly Cys Val Glu Lys Val Leu Cys Met Leu Ala Cys Trp Val Glu Asp
            370                 375                 380
Pro Asn Gly Asp Ala Phe Lys Lys His Leu Ala Arg Val Pro Asp Tyr
385                 390                 395                 400
Leu Trp Val Ser Glu Asp Gly Met Thr Met Gln Ser Phe Gly Ser Gln
                405                 410                 415
Glu Trp Asp Ala Gly Phe Ala Val Gln Ala Leu Leu Ala Thr Asn Ile
                420                 425                 430
Ile Glu Glu Ile Gly Pro Thr Phe Ala Lys Gly His Asp Phe Ile Lys
            435                 440                 445
Lys Ser Gln Val Lys Asp Asn Pro Phe Gly Asp Phe Lys Ser Met His
            450                 455                 460
Arg His Ile Ser Lys Gly Ser Trp Thr Phe Ser Asp Gln Asp His Gly
465                 470                 475                 480
Trp Gln Val Ser Asp Cys Thr Ala Glu Gly Leu Lys Cys Cys Leu Leu
                485                 490                 495
Leu Ser Met Leu Pro Pro Glu Ile Val Gly Glu Lys Met Glu Pro Glu
                500                 505                 510
Arg Leu Tyr Asp Ser Val Asn Val Leu Leu Ser Leu Gln Ser Lys Lys
            515                 520                 525
Gly Gly Leu Ala Ala Trp Glu Pro Ala Gly Ala Gln Glu Trp Leu Glu
    530                 535                 540
Leu Leu Asn Pro Thr Glu Phe Phe Ala Asp Ile Val Val Glu His Glu
545                 550                 555                 560
Tyr Val Glu Cys Thr Gly Ser Ala Ile Gln Ala Leu Val Leu Phe Lys
                565                 570                 575
```

-continued

```
Lys Leu Tyr Pro Gly His Arg Lys Lys Glu Ile Glu Asn Phe Ile Thr
            580                 585                 590

Asn Ala Val Arg Phe Leu Glu Asp Thr Gln Thr Ala Asp Gly Ser Trp
        595                 600                 605

Tyr Gly Asn Trp Gly Val Cys Phe Thr Tyr Gly Ser Trp Phe Ala Leu
    610                 615                 620

Gly Gly Leu Ala Ala Gly Lys Thr Tyr Thr Asn Cys Ala Ala Ile
625                 630                 635                 640

Arg Lys Ala Val Lys Phe Leu Leu Thr Thr Gln Arg Glu Asp Gly Gly
                645                 650                 655

Trp Gly Glu Ser Tyr Leu Ser Ser Pro Lys Lys Ile Tyr Val Pro Leu
            660                 665                 670

Glu Gly Ser Arg Ser Asn Val Val His Thr Ala Trp Ala Leu Met Gly
        675                 680                 685

Leu Ile His Ala Gly Gln Ala Asp Arg Asp Pro Met Pro Leu His Arg
    690                 695                 700

Ala Ala Lys Leu Leu Ile Asn Ser Gln Leu Glu Gly Asp Trp Pro
705                 710                 715                 720

Gln Gln Glu Ile Thr Gly Val Phe Met Lys Asn Cys Met Leu His Tyr
                725                 730                 735

Pro Met Tyr Arg Asp Ile Tyr Pro Met Trp Ala Leu Ala Glu Tyr Arg
            740                 745                 750

Arg Arg Val Pro Leu Pro Ser Thr Glu Val
        755                 760

<210> SEQ ID NO 5
<211> LENGTH: 2766
<212> TYPE: DNA
<213> ORGANISM: Glycine max

<400> SEQUENCE: 5
ttcatctccc acgcttcact ttctccctcc cctccctct ccctctccct ctccccaccc      60
cgagacctca ccctcccctc cttctccctt tcgccaccac aacgcccaac gtccacataa    120
gctagatgag atcaatctga agcaaatggt tataatttca aaattttaag agtggaggac    180
ctgtgttgtg cacgttagag tgaatcgttc aagattaatc cttaacaacc tgaccaccag    240
gaacaaccag ctatcatttt acattgaact agaaattcat ttagaagatc aaagacaaaa    300
ttttccgatt aaaacgtact taaattgaag aggggttgtt ggcattgtgc accaaaaagg    360
aaaaaaaatg tggaggttaa agatagcaga tggagggaat gatccctata tatttagcac    420
aaataatttt gtggggaggc aaacatggga gtttgattct gaggcaggta ccgctgagga    480
acgagctcaa attgaagcag ctcgtcaaaa ctttttatgaa aatcgcttca tggtcaaggc    540
ttgtggtgat cgactttggc ggtttcagat tttgagggaa ataaatttca acaaacaat    600 aagtggcgta agatagaag atgatgagaa aattacatgc gagaaaatta ggagcaccat    660
gaagagggcc actcattacc tatcgtcact acagactagt gatggtcatt ggcctgctca    720
tcttggaggt tccctctttt ttactccacc gttggtcatt tgtttatata ttacaggaca    780
tattgattct atattttcag aagagtatcg taaagagatt cttcgttaca tatattacca    840
ccagaacaaa gatggaggtt ggggactaca catagaaggt cacagtatca tgttttgcac    900
tacactcaat tatatatgca tgcgaattct tggagaagga cctaatggag tcataacaa    960 tgcttgtgct aaagcaagaa agtggattca tgatcatggt ggtgcaacac atataccttc   1020
atggggaaaa ttttggcttt cggtacttgg tatagttgat tggtgtggaa gcaacccaat   1080
```

```
gccgcctgaa ttttggatcc ttccttcttt tctccctatg catccgggta aaatgtggtg    1140
ttattgtcgg ttggtataca tgcccatgtc ttatttgtat gggaagaaat ttacgggtcc    1200
aatcacaccg ttagttgtaa atttgagaga agaacttttt attcaacctt atgatgaaaa    1260
tagttggaag aaagcacgtc ataaatgtgc aaatgaagat ctttactatc cccatcattg    1320
gatacaagat ctattatggg atagtttgta tgtattcacc gagcctcttc taaattgttg    1380
gcctttcaac aagttggtta gagaaaaggc acttcaagta caatgaaaac atattcatta    1440
tgaagacgaa aatagtcggt atattgccat cgggtgtgtg gaaaaggttc tatgtatgct    1500
tgcttgttgg gttgaagatc caaatggaga tgctttcaag aagcatcttg caaggatccc    1560
agattattta tgggtttctg aagatggaat gaccatgcag ggtattggta ctcaatcatg    1620
ggatgttggt ttcattgttc aagctttact tgctactaac cttatagatg attttggacc    1680
tacaattgca aaagctcacg atttcatcaa gaaatctcag gtaagagaaa atccttcggg    1740
agatttaaag agtatgtatc gtcacatttg taaaggctca tggacccttg ccgatagaga    1800
tcatgcatgg caagtttctg ataccactgc agaatgtttg aagtgttgtc tacttttatc    1860
agtgctgcca caagatattg tgggagaaaa aatggaactt gaaaagttac atgattcaat    1920
caatttgata ctgtcacttc agagtaaaaa tggaggtatg actgcgtggg agcccgcagg    1980
agcttataaa tggttggaac tactcaatcc tacggaattt tttgctgaca tagtagttga    2040
gcacgaatat cttgaatgca ctgcatcagc aattcaggtt ttagtgttgt tcaaaaagct    2100
ttaccctgag catagaaagg aagagataga gaacttcatt gctaaagcag taacattcat    2160
tgaagataca caattagaga atggttcttg gtatgggaat tgggcagttt gtttcactta    2220
cagctcttgg tttgcacttg gaggtctagt tgctgctggc aagacttaca caaattgtgt    2280
tactattcgt aaagctgtga aatttctact caaaatacaa aataaggacg gtgggtgggg    2340
agagagttat ctttcttgcc caaggaagat gtacgtacct cttgaaggaa gtcgatcaaa    2400
tgttgtacaa acatcatggg ctctaatggc tctaattcat gctgagcagg ctgagagaga    2460
tccaactccc cttcatcatg cagcaaagtt actcattaat tctcagttag aagatggcga    2520
ttggccccaa caagaaactc ttggagtata cttgagaaat tgcttggttc attactcatt    2580
ctatagaaat attttttccaa tgtgggcttt ggctgaatac cgcacaaatg ttttattgcc    2640
ttcctttact atttaagttg aaaaattgtg agctcaaaaa gataatgtca taccaataaa    2700
agtctagaaa aaaaaaagtt ggtaatgaag tttaataggc ttattcataa aaaaaaaaa    2760
aaaaaa                                                              2766
```

```
<210> SEQ ID NO 6
<211> LENGTH: 762
<212> TYPE: PRT
<213> ORGANISM: Glycine max

<400> SEQUENCE: 6

Met Trp Arg Leu Lys Ile Ala Asp Gly Gly Asn Asp Pro Tyr Ile Phe
  1               5                  10                  15

Ser Thr Asn Asn Phe Val Gly Arg Gln Thr Trp Glu Phe Asp Ser Glu
             20                  25                  30

Ala Gly Thr Ala Glu Glu Arg Ala Gln Ile Glu Ala Ala Arg Gln Asn
         35                  40                  45

Phe Tyr Glu Asn Arg Phe Met Val Lys Ala Cys Gly Asp Arg Leu Trp
     50                  55                  60
```

-continued

```
Arg Phe Gln Ile Leu Arg Glu Asn Asn Phe Lys Gln Thr Ile Ser Gly
 65                  70                  75                  80

Val Lys Ile Glu Asp Asp Glu Lys Ile Thr Cys Glu Lys Ile Arg Ser
                 85                  90                  95

Thr Met Lys Arg Ala Thr His Tyr Leu Ser Ser Leu Gln Thr Ser Asp
            100                 105                 110

Gly His Trp Pro Ala His Leu Gly Gly Ser Leu Phe Phe Thr Pro Pro
        115                 120                 125

Leu Val Ile Cys Leu Tyr Ile Thr Gly His Ile Asp Ser Ile Phe Ser
    130                 135                 140

Glu Glu Tyr Arg Lys Glu Ile Leu Arg Tyr Ile Tyr His Gln Asn
145                 150                 155                 160

Lys Asp Gly Gly Trp Gly Leu His Ile Glu Gly His Ser Ile Met Phe
                165                 170                 175

Cys Thr Thr Leu Asn Tyr Ile Cys Met Arg Ile Leu Gly Glu Gly Pro
            180                 185                 190

Asn Gly Gly His Asn Asn Ala Cys Ala Lys Ala Arg Lys Trp Ile His
        195                 200                 205

Asp His Gly Gly Ala Thr His Ile Pro Ser Trp Gly Lys Phe Trp Leu
    210                 215                 220

Ser Val Leu Gly Ile Val Asp Trp Cys Gly Ser Asn Pro Met Pro Pro
225                 230                 235                 240

Glu Phe Trp Ile Leu Pro Ser Phe Leu Pro Met His Pro Gly Lys Met
                245                 250                 255

Trp Cys Tyr Cys Arg Leu Val Tyr Met Pro Met Ser Tyr Leu Tyr Gly
            260                 265                 270

Lys Lys Phe Thr Gly Pro Ile Thr Pro Leu Val Val Asn Leu Arg Glu
        275                 280                 285

Glu Leu Phe Ile Gln Pro Tyr Asp Glu Asn Ser Trp Lys Lys Ala Arg
    290                 295                 300

His Lys Cys Ala Asn Glu Asp Leu Tyr Tyr Pro His His Trp Ile Gln
305                 310                 315                 320

Asp Leu Leu Trp Asp Ser Leu Tyr Val Phe Thr Glu Pro Leu Leu Asn
                325                 330                 335

Cys Trp Pro Phe Asn Lys Leu Val Arg Glu Lys Ala Leu Gln Val Thr
            340                 345                 350

Met Lys His Ile His Tyr Glu Asp Glu Asn Ser Arg Tyr Ile Ala Ile
        355                 360                 365

Gly Cys Val Glu Lys Val Leu Cys Met Leu Ala Cys Trp Val Glu Asp
    370                 375                 380

Pro Asn Gly Asp Ala Phe Lys Lys His Leu Ala Arg Ile Pro Asp Tyr
385                 390                 395                 400

Leu Trp Val Ser Glu Asp Gly Met Thr Met Gln Gly Ile Gly Thr Gln
                405                 410                 415

Ser Trp Asp Val Gly Phe Ile Val Gln Ala Leu Leu Ala Thr Asn Leu
            420                 425                 430

Ile Asp Asp Phe Gly Pro Thr Ile Ala Lys Ala His Asp Phe Ile Lys
        435                 440                 445

Lys Ser Gln Val Arg Glu Asn Pro Ser Gly Asp Phe Lys Ser Met Tyr
    450                 455                 460

Arg His Ile Cys Lys Gly Ser Trp Thr Leu Ala Asp Arg Asp His Ala
465                 470                 475                 480

Trp Gln Val Ser Asp Thr Thr Ala Glu Cys Leu Lys Cys Cys Leu Leu
```

485                 490                 495
Leu Ser Val Leu Pro Gln Asp Ile Val Gly Glu Lys Met Glu Leu Glu
            500                 505                 510

Lys Leu His Asp Ser Ile Asn Leu Ile Leu Ser Leu Gln Ser Lys Asn
        515                 520                 525

Gly Gly Met Thr Ala Trp Glu Pro Ala Gly Ala Tyr Lys Trp Leu Glu
    530                 535                 540

Leu Leu Asn Pro Thr Glu Phe Phe Ala Asp Ile Val Val Glu His Glu
545                 550                 555                 560

Tyr Leu Glu Cys Thr Ala Ser Ala Ile Gln Val Leu Val Leu Phe Lys
                565                 570                 575

Lys Leu Tyr Pro Glu His Arg Lys Glu Glu Ile Glu Asn Phe Ile Ala
            580                 585                 590

Lys Ala Val Thr Phe Ile Glu Asp Thr Gln Leu Glu Asn Gly Ser Trp
        595                 600                 605

Tyr Gly Asn Trp Ala Val Cys Phe Thr Tyr Ser Ser Trp Phe Ala Leu
    610                 615                 620

Gly Gly Leu Val Ala Ala Gly Lys Thr Tyr Thr Asn Cys Val Thr Ile
625                 630                 635                 640

Arg Lys Ala Val Lys Phe Leu Leu Lys Ile Gln Asn Lys Asp Gly Gly
                645                 650                 655

Trp Gly Glu Ser Tyr Leu Ser Cys Pro Arg Lys Met Tyr Val Pro Leu
            660                 665                 670

Glu Gly Ser Arg Ser Asn Val Val Gln Thr Ser Trp Ala Leu Met ala
        675                 680                 685

Leu Ile His Ala Glu Gln Ala Glu Arg Asp Pro Thr Pro Leu His His
    690                 695                 700

Ala Ala Lys Leu Leu Ile Asn Ser Gln Leu Glu Asp Gly Asp Trp Pro
705                 710                 715                 720

Gln Gln Glu Thr Leu Gly Val Tyr Leu Arg Asn Cys Leu Val His Tyr
                725                 730                 735

Ser Phe Tyr Arg Asn Ile Phe Pro Met Trp Ala Leu Ala Glu Tyr Arg
            740                 745                 750

Thr Asn Val Leu Leu Pro Ser Phe Thr Ile
        755                 760

<210> SEQ ID NO 7
<211> LENGTH: 2538
<212> TYPE: DNA
<213> ORGANISM: Triticum aestivum

<400> SEQUENCE: 7
gtttggggtc agcgatagtg atcgggcatt tcgtgagcta gctgagctaa ccacctgttc    60
agagagagat gtggaggctc aaggtgtccg agggtggcgg cccgtggctg cggtcggtga   120
acaacttcct cggcagggca gtgtgggagt tcgaccccga ctacggcaca ccggaggagc   180
gcgccgaggt gaagagggtg cgccgggagt tcaccgaccg ccgtttcgag aaaaaggagt   240
cgcaggatct tctcatgcgc atgcagtatg caaaagaaaa gcatcttcag gtggaccttc   300
cagccatcaa gcttgcagac agtgcacaag tcacagaaga gactttacta acatcattga   360
ggcgatgcct tagccaacat tctgctctac aagcacacga tgggcattgg gctggggact   420
tcagtggaat tttgttcatt atgcccatct tgatatttgc tctacatgtt actggatcac   480
tcaatactgt cctatcaaca gaacatcgat gtgagatttg tcgctatatt tacaaccatc   540

```
agaatgaaga tggtggttgg ggcacgcaag tgttgggtcc gagcaccatg tttggatcat    600
gcttaaacta tgttaccttta aggcttcttg gcgaggtgga aaatgatgcc ttaaccaagg    660
gacgtgcttg gattctattg cgtggaagtg caactgcaat accacaatgg ggaaagatat    720
ggctctcggt ggttggttta tatgaatggt ctggaaataa ttcgatcatt cctgagttat    780
ggcttgtccc gtattttctt ccgattcatc caggacgatt ctggtgcttt tgccggttgg    840
tttatatgcc aatgtcttat ctttacggca aaaagtttgt tggcccaatt acaccaacaa    900
tagtggcaat aagagaggag ctctatagtg tatcatacag cgagattgat tggaacaaag    960
cacgtgatac ttgtgctaag gaagaccttc gctatccacg gtcgttgctg caaaatgtta   1020
tttggacttg ccttaataaa tttgtagaac cagtgttgaa ttgttggcca atcaataagt   1080
tgagagatac agcgctgaag aacctcatga acatatacat tatgaagac gaaagcacta   1140 aatacattgg cgtatgtccg attaacaagg cactagatat gatttgttgt tggagcgagg   1200
atccaaattc agatgcactg aagttgcatc ttccaaggat ctatgactat ttatggcttg   1260
cagaagatgg catgaaagca caggtttatg atggttgtca aagctgggag cttgctttta   1320
ttgttcaagc atattgctcg acagaccttg ttaatgagtt tggtccaaca cttcggaaag   1380
cccatgagtt cattaaaagt tcacaggttc ttgagaacca tcctaacagt gaaacttatt   1440
accgccatag gtcaaaaggt tcatggacac tttcaacagc ggataatggg tggtctgtat   1500
cagattgtac tgcagaagca cttaaggcat tgttgttgtt gtcgaagatc tctcctaatc   1560
ttgtggggga tcccgtaaaa ggagaaaggt tgcatgatgc agtcgattgc ttactttctt   1620
ttatgaataa agatggcaca ttttctacat atgagtgtaa gagaactaca tctctattag   1680
aggttctcaa cccttctgaa agttttctga acattattgt cgactatcca tctgtcgaat   1740
gtacatcatc tgtgcttcag gccctaatta tgttcaaaga gctttacccct gggtaccgca   1800 aagaagagat aggaaaatgt attaaaaatg cttccaagtt cattgaggac aagcaacgaa   1860
aggatggctc atggtttggc acttggggta tatgtttcac ttatgggacg ttctttggtg   1920
taaaaggatt gattgcttct ggaagaactt acgaaaatag ttcttccata aggaaagcat   1980 gcaatttct gttgtcaaag caactaagta caggtggatg gggagagtct tatctttcta   2040
gtgaaactga ggcttatgtg gaggccacta gtcctcatgc agtgaacact gcttgggcaa   2100
tgttggcttt aatttatgct gggcaggttg aacgagatcc tactccacta tatcatgctg   2160
caaaagagtt gatcaatatg caactagaga caggagagtt tccccagcaa gaacacgttg   2220
gatgcttcaa ctgctccata tactttaatt acggcaacta tcgcaactta taccccattt   2280
gggctcttgg ggagtttcgt cgtcgactgc ttgcgaagaa ctgaaactga tgacgatgat   2340
atgtcgcttc actgctctta ggtttaggtg tggtcgtgcc tgtgacgaaa aggatgacct   2400
tagccaaact atattatata tgtgtgtgta acacatactg caataacact tacaaccaaa   2460
gtgactaatg caaacataat agcgcctgtt tggtttgtaa aaaaaaaaaa aaaaaaaaaa   2520
aaaaaaaaaa aaaaaaaa                                                  2538
```

<210> SEQ ID NO 8
<211> LENGTH: 751
<212> TYPE: PRT
<213> ORGANISM: Triticum aestivum

<400> SEQUENCE: 8

```
Met Trp Arg Leu Lys Val Ser Glu Gly Gly Pro Trp Leu Arg Ser
 1               5                  10                  15
```

-continued

```
Val Asn Asn Phe Leu Gly Arg Ala Val Trp Glu Phe Asp Pro Asp Tyr
             20                  25                  30

Gly Thr Pro Glu Glu Arg Ala Glu Val Lys Arg Val Arg Arg Glu Phe
         35                  40                  45

Thr Asp Arg Arg Phe Glu Lys Lys Glu Ser Gln Asp Leu Leu Met Arg
     50                  55                  60

Met Gln Tyr Ala Lys Glu Lys His Leu Gln Val Asp Leu Pro Ala Ile
 65                  70                  75                  80

Lys Leu Ala Asp Ser Ala Gln Val Thr Glu Glu Thr Leu Leu Thr Ser
                 85                  90                  95

Leu Arg Arg Cys Leu Ser Gln His Ser Ala Leu Gln Ala His Asp Gly
             100                 105                 110

His Trp Ala Gly Asp Phe Ser Gly Ile Leu Phe Ile Met Pro Ile Leu
         115                 120                 125

Ile Phe Ala Leu His Val Thr Gly Ser Leu Asn Thr Val Leu Ser Thr
     130                 135                 140

Glu His Arg Cys Glu Ile Cys Arg Tyr Ile Tyr Asn His Gln Asn Glu
145                 150                 155                 160

Asp Gly Gly Trp Gly Thr Gln Val Leu Gly Pro Ser Thr Met Phe Gly
                165                 170                 175

Ser Cys Leu Asn Tyr Val Thr Leu Arg Leu Leu Gly Glu Val Glu Asn
            180                 185                 190

Asp Ala Leu Thr Lys Gly Arg Ala Trp Ile Leu Leu Arg Gly Ser Ala
        195                 200                 205

Thr Ala Ile Pro Gln Trp Gly Lys Ile Trp Leu Ser Val Val Gly Leu
    210                 215                 220

Tyr Glu Trp Ser Gly Asn Asn Ser Ile Ile Pro Glu Leu Trp Leu Val
225                 230                 235                 240

Pro Tyr Phe Leu Pro Ile His Pro Gly Arg Phe Trp Cys Phe Cys Arg
                245                 250                 255

Leu Val Tyr Met Pro Met Ser Tyr Leu Tyr Gly Lys Lys Phe Val Gly
            260                 265                 270

Pro Ile Thr Pro Thr Ile Val Ala Ile Arg Glu Glu Leu Tyr Ser Val
        275                 280                 285

Ser Tyr Ser Glu Ile Asp Trp Asn Lys Ala Arg Asp Thr Cys Ala Lys
    290                 295                 300

Glu Asp Leu Arg Tyr Pro Arg Ser Leu Leu Gln Asn Val Ile Trp Thr
305                 310                 315                 320

Cys Leu Asn Lys Phe Val Glu Pro Val Leu Asn Cys Trp Pro Ile Asn
                325                 330                 335

Lys Leu Arg Asp Thr Ala Leu Lys Asn Leu Met Lys His Ile His Tyr
            340                 345                 350

Glu Asp Glu Ser Thr Lys Tyr Ile Gly Val Cys Pro Ile Asn Lys Ala
        355                 360                 365

Leu Asp Met Ile Cys Cys Trp Ser Glu Asp Pro Asn Ser Asp Ala Leu
    370                 375                 380

Lys Leu His Leu Pro Arg Ile Tyr Asp Tyr Leu Trp Leu Ala Glu Asp
385                 390                 395                 400

Gly Met Lys Ala Gln Val Tyr Asp Gly Cys Gln Ser Trp Glu Leu Ala
                405                 410                 415

Phe Ile Val Gln Ala Tyr Cys Ser Thr Asp Leu Val Asn Glu Phe Gly
            420                 425                 430

Pro Thr Leu Arg Lys Ala His Glu Phe Ile Lys Ser Ser Gln Val Leu
```

```
                435             440             445
Glu Asn His Pro Asn Ser Glu Thr Tyr Tyr Arg His Arg Ser Lys Gly
    450                 455                 460
Ser Trp Thr Leu Ser Thr Ala Asp Asn Gly Trp Ser Val Ser Asp Cys
465                 470                 475                 480
Thr Ala Glu Ala Leu Lys Ala Leu Leu Leu Ser Lys Ile Ser Pro
            485                 490                 495
Asn Leu Val Gly Asp Pro Val Lys Gly Glu Arg Leu His Asp Ala Val
            500                 505                 510
Asp Cys Leu Leu Ser Phe Met Asn Lys Asp Gly Thr Phe Ser Thr Tyr
            515                 520                 525
Glu Cys Lys Arg Thr Thr Ser Leu Leu Glu Val Leu Asn Pro Ser Glu
    530                 535                 540
Ser Phe Leu Asn Ile Ile Val Asp Tyr Pro Ser Val Glu Cys Thr Ser
545                 550                 555                 560
Ser Val Leu Gln Ala Leu Ile Met Phe Lys Glu Leu Tyr Pro Gly Tyr
                565                 570                 575
Arg Lys Glu Glu Ile Gly Lys Cys Ile Lys Asn Ala Ser Lys Phe Ile
            580                 585                 590
Glu Asp Lys Gln Arg Lys Asp Gly Ser Trp Phe Gly Thr Trp Gly Ile
            595                 600                 605
Cys Phe Thr Tyr Gly Thr Phe Phe Gly Val Lys Gly Leu Ile Ala Ser
    610                 615                 620
Gly Arg Thr Tyr Glu Asn Ser Ser Ile Arg Lys Ala Cys Asn Phe
625                 630                 635                 640
Leu Leu Ser Lys Gln Leu Ser Thr Gly Gly Trp Gly Glu Ser Tyr Leu
            645                 650                 655
Ser Ser Glu Thr Glu Ala Tyr Val Glu Ala Thr Ser Pro His Ala Val
            660                 665                 670
Asn Thr Ala Trp Ala Met Leu Ala Leu Ile Tyr Ala Gly Gln Val Glu
            675                 680                 685
Arg Asp Pro Thr Pro Leu Tyr His Ala Ala Lys Glu Leu Ile Asn Met
    690                 695                 700
Gln Leu Glu Thr Gly Glu Phe Pro Gln Gln Glu His Val Gly Cys Phe
705                 710                 715                 720
Asn Cys Ser Ile Tyr Phe Asn Tyr Gly Asn Tyr Arg Asn Leu Tyr Pro
                725                 730                 735
Ile Trp Ala Leu Gly Glu Phe Arg Arg Arg Leu Leu Ala Lys Asn
            740                 745                 750

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence:PCR primer

<400> SEQUENCE: 9
tcaaggagaa aaaccccgg atccatgtgg aggctgaaga tagcag                    46

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence:PCR primer
```

-continued

```
<400> SEQUENCE: 10
tcaaggagaa aaacccggg atccatgtgg aggttaaaga tagcag                46

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence:PCR primer

<400> SEQUENCE: 11
ggccagtgaa ttgtaatacg actcactata gggcg                           35

<210> SEQ ID NO 12
<211> LENGTH: 761
<212> TYPE: PRT
<213> ORGANISM: Panax ginseng

<400> SEQUENCE: 12
```

| Met | Trp | Arg | Leu | Met | Thr | Ala | Lys | Gly | Gly | Asn | Asp | Pro | Tyr | Leu | Tyr |
|---|---|---|---|---|---|---|---|---|---|---|---|---|---|---|---|
| 1 | | | | 5 | | | | | 10 | | | | | 15 | |

| Ser | Thr | Asn | Asn | Phe | Ile | Gly | Arg | Gln | Thr | Trp | Glu | Phe | Asp | Pro | Asp |
|---|---|---|---|---|---|---|---|---|---|---|---|---|---|---|---|
| | | | 20 | | | | | 25 | | | | | 30 | | |

| Tyr | Gly | Thr | Pro | Ala | Glu | Arg | Ala | Glu | Val | Glu | Glu | Ala | Arg | Leu | His |
|---|---|---|---|---|---|---|---|---|---|---|---|---|---|---|---|
| | | 35 | | | | | 40 | | | | | 45 | | | |

| Phe | Trp | Asn | Asn | Arg | Tyr | Gln | Val | Lys | Pro | Ser | Ser | Asp | Val | Leu | Trp |
|---|---|---|---|---|---|---|---|---|---|---|---|---|---|---|---|
| | 50 | | | | | 55 | | | | | 60 | | | | |

| Arg | Met | Gln | Phe | Leu | Lys | Glu | Lys | Asn | Phe | Lys | Gln | Ile | Ile | Pro | Gln |
|---|---|---|---|---|---|---|---|---|---|---|---|---|---|---|---|
| 65 | | | | | 70 | | | | | 75 | | | | | 80 |

| Val | Lys | Val | Glu | Asp | Gly | Glu | Glu | Ile | Thr | Tyr | Glu | Ala | Ala | Thr | Thr |
|---|---|---|---|---|---|---|---|---|---|---|---|---|---|---|---|
| | | | | 85 | | | | | 90 | | | | | 95 | |

| Thr | Leu | Arg | Arg | Ala | Val | His | Tyr | Phe | Ser | Ala | Leu | Gln | Ala | Asp | Asp |
|---|---|---|---|---|---|---|---|---|---|---|---|---|---|---|---|
| | | | 100 | | | | | 105 | | | | | 110 | | |

| Gly | His | Trp | Pro | Ala | Glu | Asn | Ala | Gly | Pro | Leu | Phe | Phe | Leu | Pro | Pro |
|---|---|---|---|---|---|---|---|---|---|---|---|---|---|---|---|
| | | 115 | | | | | 120 | | | | | 125 | | | |

| Leu | Val | Met | Cys | Leu | Tyr | Ile | Thr | Gly | His | Leu | Asn | Thr | Val | Phe | Pro |
|---|---|---|---|---|---|---|---|---|---|---|---|---|---|---|---|
| | 130 | | | | | 135 | | | | | 140 | | | | |

| Ala | Glu | His | Arg | Ile | Glu | Ile | Leu | Arg | Tyr | Ile | Tyr | Cys | His | Gln | Asn |
|---|---|---|---|---|---|---|---|---|---|---|---|---|---|---|---|
| 145 | | | | | 150 | | | | | 155 | | | | | 160 |

| Asp | Asp | Gly | Gly | Trp | Gly | Leu | His | Ile | Glu | Gly | His | Ser | Thr | Met | Phe |
|---|---|---|---|---|---|---|---|---|---|---|---|---|---|---|---|
| | | | | 165 | | | | | 170 | | | | | 175 | |

| Cys | Thr | Ala | Leu | Ser | Tyr | Ile | Cys | Met | Arg | Ile | Leu | Gly | Glu | Gly | Arg |
|---|---|---|---|---|---|---|---|---|---|---|---|---|---|---|---|
| | | | 180 | | | | | 185 | | | | | 190 | | |

| Asp | Gly | Gly | Glu | Asn | Asn | Ala | Cys | Ala | Arg | Ala | Arg | Lys | Trp | Ile | Leu |
|---|---|---|---|---|---|---|---|---|---|---|---|---|---|---|---|
| | | 195 | | | | | 200 | | | | | 205 | | | |

| Asp | His | Gly | Ser | Val | Thr | Ala | Ile | Pro | Ser | Trp | Gly | Lys | Thr | Trp | Leu |
|---|---|---|---|---|---|---|---|---|---|---|---|---|---|---|---|
| | 210 | | | | | 215 | | | | | 220 | | | | |

| Ser | Ile | Leu | Gly | Leu | Phe | Asp | Trp | Ser | Gly | Ser | Asn | Pro | Met | Pro | Pro |
|---|---|---|---|---|---|---|---|---|---|---|---|---|---|---|---|
| 225 | | | | | 230 | | | | | 235 | | | | | 240 |

| Glu | Phe | Trp | Ile | Leu | Pro | Pro | Phe | Leu | Pro | Met | His | Pro | Ala | Lys | Met |
|---|---|---|---|---|---|---|---|---|---|---|---|---|---|---|---|
| | | | | 245 | | | | | 250 | | | | | 255 | |

| Trp | Cys | Tyr | Cys | Arg | Met | Val | Tyr | Met | Pro | Met | Ser | Tyr | Leu | Tyr | Gly |
|---|---|---|---|---|---|---|---|---|---|---|---|---|---|---|---|
| | | | 260 | | | | | 265 | | | | | 270 | | |

| Lys | Arg | Phe | Val | Gly | Pro | Ile | Thr | Pro | Leu | Ile | Leu | Gln | Leu | Arg | Glu |
|---|---|---|---|---|---|---|---|---|---|---|---|---|---|---|---|
| | | 275 | | | | | 280 | | | | | 285 | | | |

| Glu | Leu | Tyr | Ala | Gln | Ala | Tyr | Asp | Glu | Ile | Asn | Trp | Arg | Lys | Val | Arg |
|---|---|---|---|---|---|---|---|---|---|---|---|---|---|---|---|

-continued

```
                 290                 295                 300
His Asn Cys Ala Lys Glu Asp Leu Tyr Tyr Pro His Pro Leu Ile Gln
305                 310                 315                 320

Asp Leu Met Trp Asp Ser Leu Tyr Ile Phe Thr Glu Pro Phe Leu Thr
                325                 330                 335

Arg Trp Pro Phe Asn Lys Leu Arg Glu Lys Ala Leu Gln Thr Thr Met
                340                 345                 350

Lys His Ile His Tyr Glu Asp Glu Asn Ser Arg Tyr Ile Thr Ile Gly
            355                 360                 365

Cys Val Glu Lys Val Leu Cys Met Leu Ala Cys Trp Val Glu Asp Pro
370                 375                 380

Asn Gly Asp Tyr Phe Lys Gln His Leu Ala Arg Ile Pro Asp Tyr Ile
385                 390                 395                 400

Trp Val Ala Glu Asp Gly Met Lys Met Gln Ser Phe Gly Ser Gln Glu
                405                 410                 415

Trp Asp Thr Gly Phe Ala Ile Gln Ala Leu Leu Ala Ser Asp Leu Ile
                420                 425                 430

Asp Glu Ile Arg Pro Thr Leu Met Lys Gly His Asp Phe Ile Lys Lys
            435                 440                 445

Ser Gln Val Lys Glu Asn Pro Ser Gly Asp Phe Lys Ser Met His Arg
450                 455                 460

His Ile Ser Lys Gly Ser Trp Thr Phe Ser Asp Gln Asp His Gly Trp
465                 470                 475                 480

Gln Val Ser Asp Cys Thr Ala Glu Ala Leu Lys Cys Cys Leu Leu Phe
                485                 490                 495

Ser Arg Met Pro Thr Glu Ile Val Gly Asp Lys Met Glu Asp Asn Gln
                500                 505                 510

Leu Phe Asp Ala Val Asn Met Leu Leu Ser Leu Gln Ser Lys Asn Gly
            515                 520                 525

Gly Leu Ala Ala Trp Glu Pro Ala Gly Ser Ser Glu Trp Leu Glu Leu
            530                 535                 540

Leu Asn Pro Thr Glu Phe Phe Glu Asp Ile Val Ile Glu His Glu Tyr
545                 550                 555                 560

Val Glu Cys Thr Ser Ser Ala Ile Gln Ala Met Val Met Phe Lys Lys
                565                 570                 575

Leu Tyr Pro Gly His Arg Lys Lys Glu Ile Glu Val Ser Ile Thr Asn
                580                 585                 590

Ala Val Gln Tyr Leu Glu Asp Ile Gln Met Pro Asp Gly Ser Trp Tyr
            595                 600                 605

Gly Asn Trp Gly Val Cys Phe Thr Tyr Gly Thr Trp Phe Ala Met Gly
610                 615                 620

Gly Leu Thr Ala Ala Gly Lys Thr Tyr Asn Asn Cys Gln Thr Leu His
625                 630                 635                 640

Lys Ala Val Asp Phe Leu Ile Lys Ser Gln Arg Ser Asp Gly Gly Trp
                645                 650                 655

Gly Glu Ser Tyr Leu Ser Cys Pro Asn Lys Glu Tyr Thr Pro Leu Glu
                660                 665                 670

Gly Asn Arg Ser Asn Leu Val His Thr Ser Trp Ala Met Met Gly Leu
            675                 680                 685

Ile His Ser Arg Gln Ala Glu Arg Asp Pro Thr Pro Leu His Arg Ala
            690                 695                 700

Ala Lys Leu Leu Ile Asn Ser Gln Met Glu Ser Gly Asp Phe Pro Gln
705                 710                 715                 720
```

-continued

Gln Glu Ile Thr Gly Val Phe Met Lys Asn Cys Met Leu His Tyr Ala
                725                 730                 735

Ala Ser Arg Asn Ile Tyr Pro Leu Trp Ala Leu Ala Glu Tyr Arg Lys
            740                 745                 750

Asn Val Arg Leu Pro Ser Lys Ser Val
        755                 760

<210> SEQ ID NO 13
<211> LENGTH: 763
<212> TYPE: PRT
<213> ORGANISM: Panax ginseng

<400> SEQUENCE: 13

Met Trp Lys Leu Lys Ile Ala Glu Gly Asn Lys Asn Asp Pro Tyr Leu
  1               5                  10                  15

Tyr Ser Thr Asn Asn Phe Val Gly Arg Gln Thr Trp Glu Phe Asp Pro
             20                  25                  30

Asp Tyr Val Ala Ser Pro Gly Glu Leu Glu Glu Val Glu Gln Val Arg
         35                  40                  45

Arg Gln Phe Trp Asp Asn Arg Tyr Gln Val Lys Pro Ser Gly Asp Leu
     50                  55                  60

Leu Trp Arg Met Gln Phe Leu Arg Glu Lys Asn Phe Arg Gln Thr Ile
 65                  70                  75                  80

Pro Gln Val Lys Val Gly Asp Glu Ala Val Thr Tyr Glu Ala Ala
                 85                  90                  95

Thr Thr Thr Leu Arg Arg Ala Val His Phe Phe Ser Ala Leu Gln Ala
                100                 105                 110

Ser Asp Gly His Trp Pro Ala Glu Asn Ser Gly Pro Leu Phe Phe Leu
            115                 120                 125

Pro Pro Leu Val Met Cys Val Tyr Ile Thr Gly His Leu Asp Thr Val
        130                 135                 140

Phe Pro Ala Glu His Arg Lys Glu Ile Leu Arg Tyr Ile Tyr Cys His
145                 150                 155                 160

Gln Asn Glu Asp Gly Gly Trp Gly Leu His Ile Glu Gly His Ser Thr
                165                 170                 175

Met Phe Cys Thr Thr Leu Ser Tyr Ile Cys Met Arg Ile Leu Gly Glu
            180                 185                 190

Gly Pro Asp Gly Gly Val Asn Asn Ala Cys Ala Arg Gly Arg Lys Trp
        195                 200                 205

Ile Leu Asp His Gly Ser Val Thr Ala Ile Pro Ser Trp Gly Lys Thr
    210                 215                 220

Trp Leu Ser Ile Leu Gly Val Tyr Glu Trp Ile Gly Ser Asn Pro Met
225                 230                 235                 240

Pro Pro Glu Phe Trp Ile Leu Pro Ser Phe Leu Pro Met His Pro Ala
                245                 250                 255

Lys Met Trp Cys Tyr Cys Arg Met Val Tyr Met Pro Met Ser Tyr Leu
            260                 265                 270

Tyr Gly Lys Arg Phe Val Gly Pro Ile Thr Pro Leu Ile Leu Gln Leu
        275                 280                 285

Arg Glu Glu Leu Tyr Gly Gln Pro Tyr Asn Glu Ile Asn Trp Arg Lys
    290                 295                 300

Thr Arg Arg Val Cys Ala Lys Glu Asp Ile Tyr Tyr Pro His Pro Leu
305                 310                 315                 320

Ile Gln Asp Leu Leu Trp Asp Ser Leu Tyr Val Leu Thr Glu Pro Leu

```
                        325                 330                 335
Leu Thr Arg Trp Pro Phe Asn Lys Leu Arg Glu Lys Ala Leu Gln Thr
                340                 345                 350
Thr Met Lys His Ile His Tyr Glu Asp Glu Asn Ser Arg Tyr Ile Thr
            355                 360                 365
Ile Gly Cys Val Glu Lys Val Leu Cys Met Leu Val Cys Trp Val Glu
        370                 375                 380
Asp Pro Asn Gly Asp Tyr Phe Arg Lys His Leu Ala Arg Ile Pro Asp
385                 390                 395                 400
Tyr Ile Trp Val Ala Glu Asp Gly Met Lys Met Gln Ser Phe Gly Ser
                405                 410                 415
Gln Glu Trp Asp Thr Gly Phe Ser Ile Gln Ala Leu Leu Asp Ser Asp
                420                 425                 430
Leu Thr His Glu Ile Gly Pro Thr Leu Met Lys Gly His Asp Phe Ile
            435                 440                 445
Lys Lys Ser Gln Val Lys Asp Asn Pro Ser Gly Asp Phe Lys Ser Met
        450                 455                 460
Tyr Arg His Ile Ser Lys Gly Ser Trp Thr Phe Ser Asp Gln Asp His
465                 470                 475                 480
Gly Trp Gln Val Ser Asp Cys Thr Ala Glu Gly Leu Lys Cys Cys Leu
                485                 490                 495
Ile Phe Ser Thr Met Pro Glu Glu Ile Val Gly Lys Lys Ile Lys Pro
                500                 505                 510
Glu Arg Leu Tyr Asp Ser Val Asn Val Leu Leu Ser Leu Gln Arg Lys
            515                 520                 525
Asn Gly Gly Leu Ser Ala Trp Glu Pro Ala Gly Ala Gln Glu Trp Leu
        530                 535                 540
Glu Leu Leu Asn Pro Thr Glu Phe Phe Ala Asp Ile Val Ile Glu His
545                 550                 555                 560
Glu Tyr Val Glu Cys Thr Ser Ser Ala Ile Gln Ala Leu Val Leu Phe
                565                 570                 575
Lys Lys Leu Tyr Pro Gly His Arg Lys Lys Glu Ile Asp Asn Phe Ile
            580                 585                 590
Thr Asn Ala Val Arg Tyr Leu Glu Asp Thr Gln Met Pro Asp Gly Ser
        595                 600                 605
Trp Tyr Gly Asn Trp Gly Val Cys Phe Thr Tyr Gly Ser Trp Phe Ala
    610                 615                 620
Leu Gly Gly Leu Ala Ala Ala Gly Lys Thr Tyr Tyr Asn Cys Ala Ala
625                 630                 635                 640
Val Arg Lys Ala Val Glu Phe Leu Leu Lys Ser Gln Met Asp Asp Gly
                645                 650                 655
Gly Trp Gly Glu Ser Tyr Leu Ser Cys Pro Lys Lys Val Tyr Val Pro
            660                 665                 670
Leu Glu Gly Asn Arg Ser Asn Leu Val His Thr Gly Trp Ala Leu Met
        675                 680                 685
Gly Leu Ile His Ser Glu Gln Ala Glu Arg Asp Pro Thr Pro Leu His
    690                 695                 700
Arg Ala Ala Lys Leu Leu Ile Asn Ser Gln Met Glu Asp Gly Asp Phe
705                 710                 715                 720
Pro Gln Gln Glu Ile Ser Gly Val Phe Met Lys Asn Cys Met Leu His
                725                 730                 735
```

```
Tyr Ala Ala Tyr Arg Asn Ile Tyr Pro Leu Trp Ala Leu Ala Glu Tyr
            740                 745                 750
Arg Arg Arg Val Pro Leu Pro Ser Leu Gly Thr
            755                 760
```